US012336704B2

(12) United States Patent
Niver et al.

(10) Patent No.: US 12,336,704 B2
(45) Date of Patent: Jun. 24, 2025

(54) APPARATUS AND METHODS FOR JOINING BONES

(71) Applicant: Medline Industries, LP, Northfield, IL (US)

(72) Inventors: Ryan Niver, Glenview, IL (US); Natan Pheil, Highland Park, IL (US); Samuel Nader, Arlington Heights, IL (US); Dinesh Koka, Winter Park, FL (US)

(73) Assignee: Medline Industries, LP, Northfield, IL (US)

( * ) Notice: Subject to any disclaimer, the term of this patent is extended or adjusted under 35 U.S.C. 154(b) by 295 days.

(21) Appl. No.: 18/154,788

(22) Filed: Jan. 13, 2023

(65) Prior Publication Data
US 2024/0237980 A1 Jul. 18, 2024

(51) Int. Cl.
*A61B 17/064* (2006.01)
*A61B 17/16* (2006.01)
*A61B 17/17* (2006.01)

(52) U.S. Cl.
CPC ...... *A61B 17/0642* (2013.01); *A61B 17/1615* (2013.01); *A61B 2017/0641* (2013.01); *A61B 17/1682* (2013.01); *A61B 17/1714* (2013.01); *A61B 17/1728* (2013.01); *A61B 17/1739* (2013.01); *A61B 17/1775* (2016.11); *A61B 17/1782* (2016.11)

(58) Field of Classification Search
CPC ............ A61B 17/0642; A61B 17/1615; A61B 17/1728; A61B 17/17; A61B 17/1775; A61B 17/0641; A61B 17/0648; A61B 17/064; A61B 17/068; A61B 17/0682; A61B 17/1714; A61B 17/1682; A61B 17/1739; A61B 17/1782; A61B 2017/0641; A61B 2017/0648; A61B 2017/564; A61B 2017/0645
USPC ..................................................... 606/75, 96
See application file for complete search history.

(56) References Cited

U.S. PATENT DOCUMENTS

| 294,777 A | 3/1884 | Forbes |
| 324,126 A | 8/1885 | Gay |

(Continued)

FOREIGN PATENT DOCUMENTS

| EP | 0127994 | 12/1984 |
| FR | 2628312 | 9/1989 |

(Continued)

OTHER PUBLICATIONS

Memometal Inc. USA, Easy Clip SI brochure, Aug. 12, 2009.

(Continued)

*Primary Examiner* — Marcela I. Shirsat
(74) *Attorney, Agent, or Firm* — Fitch, Even, Tabin & Flannery LLP

(57) ABSTRACT

Apparatus and methods are described for use in securing a first bone relative to a second bone using a pair of surgical staples or, alternatively, a surgical staple and a bone screw. When a pair of staples are used, one of the legs of one of the staples may pass between the legs of the another of the staples. When a staple and a bone screw are used, the bone screw may pass between the legs of the staple. A guide tool can be used during the drilling of the holes for the legs of the staples or the legs of the staple and a bone screw. The guide tool provides guides for drilling guide holes for the staples or for the screw and staple.

9 Claims, 24 Drawing Sheets

(56) References Cited

U.S. PATENT DOCUMENTS

| | | |
|---|---|---|
| D28,350 S | 3/1898 | Reuter |
| D29,472 S | 10/1898 | Hughes et al. |
| 1,257,807 A | 2/1918 | Carrell |
| 1,354,737 A | 10/1920 | Frisk |
| 1,639,530 A | 8/1927 | Payson |
| 2,067,359 A | 1/1937 | Tumminello |
| 2,174,708 A | 10/1939 | Sears |
| 3,154,999 A | 11/1964 | Stewart |
| 3,316,794 A | 5/1967 | Dixon |
| 3,564,663 A | 2/1971 | Roberts |
| 3,584,347 A | 6/1971 | Klenz |
| 3,787,608 A | 1/1974 | Colby |
| 3,821,919 A | 7/1974 | Knohl |
| 3,824,995 A | 7/1974 | Getscher |
| 3,940,844 A | 3/1976 | Colby |
| 3,960,147 A | 6/1976 | Murray |
| D243,365 S | 2/1977 | Cross |
| 4,263,903 A | 4/1981 | Griggs |
| 4,454,875 A | 6/1984 | Pratt |
| D281,814 S | 12/1985 | Pratt |
| 4,565,193 A | 1/1986 | Streli |
| 4,570,623 A | 2/1986 | Ellison |
| 4,592,346 A | 6/1986 | Jurgutis |
| D286,442 S | 10/1986 | Korthoff |
| 4,799,481 A | 1/1989 | Transue |
| 4,848,328 A | 7/1989 | Laboureau |
| 5,179,964 A | 1/1993 | Cook |
| 5,263,973 A | 11/1993 | Cook |
| 5,449,359 A | 9/1995 | Groiso |
| 5,454,814 A | 10/1995 | Comte |
| 5,662,655 A | 9/1997 | Laboureau |
| 5,674,222 A | 10/1997 | Berger |
| 5,785,713 A | 7/1998 | Jobe |
| 5,853,414 A | 12/1998 | Groiso |
| 5,941,890 A | 8/1999 | Voegele |
| 6,001,110 A | 12/1999 | Adams |
| 6,066,142 A * | 5/2000 | Serbousek ......... A61B 17/1728 606/70 |
| 6,120,511 A | 9/2000 | Chan |
| 6,187,009 B1 | 2/2001 | Herzog |
| 6,325,805 B1 | 12/2001 | Ogilvie |
| 6,336,928 B1 | 1/2002 | Guerin |
| 6,401,306 B1 | 6/2002 | Hanten |
| 6,652,592 B1 | 11/2003 | Grooms |
| 6,767,356 B2 | 7/2004 | Kanner |
| 6,773,437 B2 | 8/2004 | Ogilvie |
| 7,108,697 B2 | 9/2006 | Mingozzi |
| D572,363 S | 7/2008 | Menn |
| D587,370 S | 2/2009 | Coillard-Lavirotte |
| D596,294 S | 7/2009 | Coillard-Lavirotte |
| 7,722,610 B2 | 5/2010 | Viola |
| 7,794,475 B2 | 9/2010 | Hess |
| 7,824,426 B2 | 11/2010 | Racenet |
| 8,021,389 B2 | 9/2011 | Molz, IV |
| 8,360,297 B2 | 1/2013 | Shelton, IV |
| 8,366,748 B2 | 2/2013 | Kleiner |
| 8,393,517 B2 | 3/2013 | Milo |
| 8,584,853 B2 | 11/2013 | Knight |
| 8,596,514 B2 | 12/2013 | Miller |
| 8,679,154 B2 | 3/2014 | Smith |
| D705,930 S | 5/2014 | Cheney |
| 8,720,766 B2 | 5/2014 | Hess |
| D707,357 S | 6/2014 | Cheney |
| 8,808,325 B2 | 8/2014 | Hess |
| D728,103 S | 4/2015 | Katchis |
| 9,039,737 B2 | 5/2015 | Vold |
| 9,198,769 B2 | 12/2015 | Perrow |
| 9,254,180 B2 | 2/2016 | Huitema |
| 9,295,463 B2 | 3/2016 | Viola |
| 9,339,268 B2 | 5/2016 | Fox |
| 9,402,624 B1 | 8/2016 | Scott |
| 9,433,452 B2 | 9/2016 | Weiner |
| 9,463,260 B2 | 10/2016 | Stopek |
| 9,486,212 B2 | 11/2016 | Miller |
| D780,311 S | 2/2017 | Cheney |
| 9,743,926 B2 | 8/2017 | Fox |
| 9,855,036 B2 | 1/2018 | Palmer |
| 9,901,338 B2 | 2/2018 | Anderson |
| D826,405 S | 8/2018 | Shelton, IV |
| 10,058,366 B2 | 8/2018 | Bouduban |
| 10,064,619 B2 | 9/2018 | Palmer |
| 10,064,623 B2 | 9/2018 | Soutorine |
| 10,085,743 B2 | 10/2018 | Roedl |
| 10,105,134 B2 | 10/2018 | Biedermann |
| 10,117,647 B2 | 11/2018 | Cheney |
| 10,130,358 B2 | 11/2018 | Palmer |
| 10,166,022 B2 | 1/2019 | Early |
| D840,035 S | 2/2019 | Weiner |
| 10,238,382 B2 | 3/2019 | Terrill |
| 10,307,156 B1 | 6/2019 | Blair |
| D857,199 S | 8/2019 | Cheney |
| 10,610,218 B2 | 4/2020 | Palmer et al. |
| D886,299 S | 6/2020 | Cundiff |
| D895,113 S | 9/2020 | Blair |
| 10,779,816 B2 | 9/2020 | Goldstein |
| 10,820,902 B2 | 11/2020 | Cheney |
| 10,874,389 B2 | 12/2020 | Biedermann |
| 10,918,484 B2 | 2/2021 | Ellington et al. |
| 10,945,725 B2 | 3/2021 | Hollis |
| 10,987,101 B2 | 4/2021 | Ducharme |
| 11,000,323 B2 | 5/2021 | Stamp |
| 11,006,949 B2 | 5/2021 | Daniel |
| 11,020,110 B1 | 6/2021 | Blair |
| 11,090,043 B2 | 8/2021 | Biedermann |
| 11,116,499 B1 | 9/2021 | Blair |
| 11,278,278 B2 | 3/2022 | Biedermann |
| 11,284,886 B2 | 3/2022 | Hartdegen |
| D957,636 S | 7/2022 | Blair |
| 11,553,952 B2 | 1/2023 | Hammann |
| 11,596,398 B2 | 3/2023 | Wahl |
| 11,642,124 B2 | 5/2023 | Maclure et al. |
| 11,653,913 B2 | 5/2023 | Goldstein et al. |
| 11,684,359 B2 | 6/2023 | Biedermann |
| 11,911,036 B2 | 2/2024 | Reed |
| D1,017,038 S | 3/2024 | Bushko |
| 11,937,819 B2 | 3/2024 | Pheil |
| 2003/0225423 A1 | 12/2003 | Huitema |
| 2004/0193188 A1 | 9/2004 | Francese |
| 2005/0021035 A1 | 1/2005 | Groiso |
| 2005/0288707 A1 | 12/2005 | De Canniere |
| 2006/0058802 A1 | 3/2006 | Kofoed |
| 2007/0233113 A1 | 10/2007 | Kaelblein |
| 2007/0270906 A1 | 11/2007 | Molz |
| 2007/0276388 A1 | 11/2007 | Robertson |
| 2008/0147068 A1 | 6/2008 | Hashimoto |
| 2009/0005809 A1 | 1/2009 | Hess |
| 2011/0022099 A1 | 1/2011 | Ashman |
| 2013/0231667 A1 | 9/2013 | Taylor |
| 2013/0345752 A1 | 12/2013 | Hendren |
| 2014/0276830 A1 | 9/2014 | Cheney |
| 2014/0277516 A1 | 9/2014 | Miller |
| 2014/0358187 A1 | 12/2014 | Taber |
| 2015/0133940 A1 | 5/2015 | Palmer |
| 2015/0313592 A1 | 11/2015 | Coillard-Lavirotte |
| 2017/0000482 A1 | 1/2017 | Averous |
| 2017/0252036 A1 | 9/2017 | Palmer et al. |
| 2018/0271521 A1 | 9/2018 | Wahl |
| 2018/0344316 A1 | 12/2018 | Palmer |
| 2019/0046182 A1 | 2/2019 | Krumme |
| 2019/0069892 A1 | 3/2019 | Biedermann |
| 2019/0105040 A1 | 4/2019 | Gordon |
| 2019/0115040 A1 | 4/2019 | Kamdar et al. |
| 2020/0000046 A1 | 1/2020 | Orschulik |
| 2020/0038076 A1 | 2/2020 | Amis |
| 2020/0046345 A1 | 2/2020 | Zink |
| 2021/0298748 A1 * | 9/2021 | Campbell .......... A61B 17/0642 |
| 2021/0330324 A1 | 10/2021 | Biedermann |
| 2021/0386422 A1 | 12/2021 | Maclure |
| 2022/0211368 A1 | 7/2022 | Hartdegen |
| 2023/0000488 A1 | 1/2023 | Palmer |
| 2023/0060073 A1 * | 2/2023 | Niver ................ A61B 17/0642 |
| 2023/0172647 A1 | 6/2023 | Knight |
| 2023/0200809 A1 | 6/2023 | Wahl |

(56) References Cited

U.S. PATENT DOCUMENTS

FOREIGN PATENT DOCUMENTS

| | | |
|---|---|---|
| FR | 2694696 | 2/1994 |
| FR | 3023468 | 1/2016 |
| GB | 793126 | 4/1958 |
| IL | 64726 | 2/1985 |
| WO | 9616603 | 6/1996 |
| WO | 2006077878 | 7/2006 |
| WO | 201288575 | 7/2012 |

OTHER PUBLICATIONS

Stryker, EasyClip Osteosynthesis Compression Staples brochure, bearing a copyright date of 2015.
U. Rethnam et al., "Mechanical Characteristics of Three Staples Commonly Used in Foot Surgery," Journal of Foot and Ankle Research (Feb. 25, 2009).

* cited by examiner

APPARATUS AND METHODS FOR JOINING BONES

FIELD

Apparatus and methods for joining or fusing one bone or two bones together are described herein and, more specifically, apparatus and methods for drilling guide holes in bones for receiving surgical staples or a surgical staple and a bone screw.

BACKGROUND

Screws are commonly used for joining or fusing two bones or bone pieces together. The screw or screws may cross a joint, fracture or osteotomy. For example, screws can be used to fuse metatarsal phalangeal (MTP) joints to relieve pain. In another example, screws can be used in a Lapidus procedure to fuse the joint between the first metatarsal bone and the medial cuneiform. Instead of screws, fusions can be made using compression staples. A problem with using screws or staples, particularly where multiple such fasteners are used in a single procedure, is that often guide holes for receiving the screws or legs of the staples are drilled free-hand. Although suitable fusions can be made using holes that are drilled free-hand, this can be time consuming and potentially prone to errors in the relative positioning and orientating of the staple legs or screw. The guide tools and methods described herein can address these problems.

DETAILED DESCRIPTION

As described herein and shown in FIGS. 1-37, apparatus and methods are disclosed for use in securing a first bone relative to a second bone using a pair of surgical staples or, alternatively, a surgical staple and a bone screw. When a pair of staples are used, advantageously at least one of the legs of one of the staples passes between the legs of the another of the staples. If the legs of the staple are coplanar, then this can beneficially result in intersecting planes of securement. When a staple and a bone screw are used, advantageously the bone screw passes between the legs of the staple. This can beneficially result in the bone screw intersecting a plane of the legs of the staple. A guide tool can be used during the drilling of the holes for the legs of the staples or the legs of the staple and a bone screw. Advantageously, the guide tool provides guides for drilling the guide holes such that the guides can be fixed relative to each other to improve accuracy during drilling and make the fusion procedure faster, simpler and readily reproducible.

Figure 10:
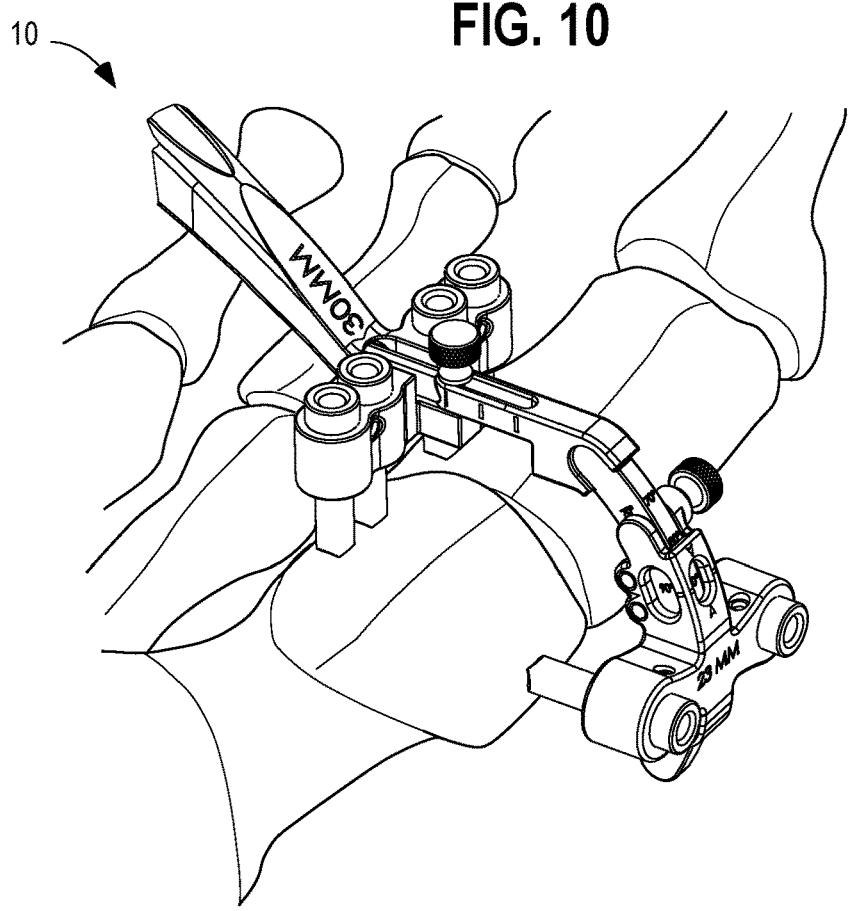
FIG. 10 is another perspective view of an operative portion of the guide tool of FIG. 1 positioned adjacent a bone in before guide holes have been drilled in the bone and before staples inserted into the guide holes.
Figure 11:
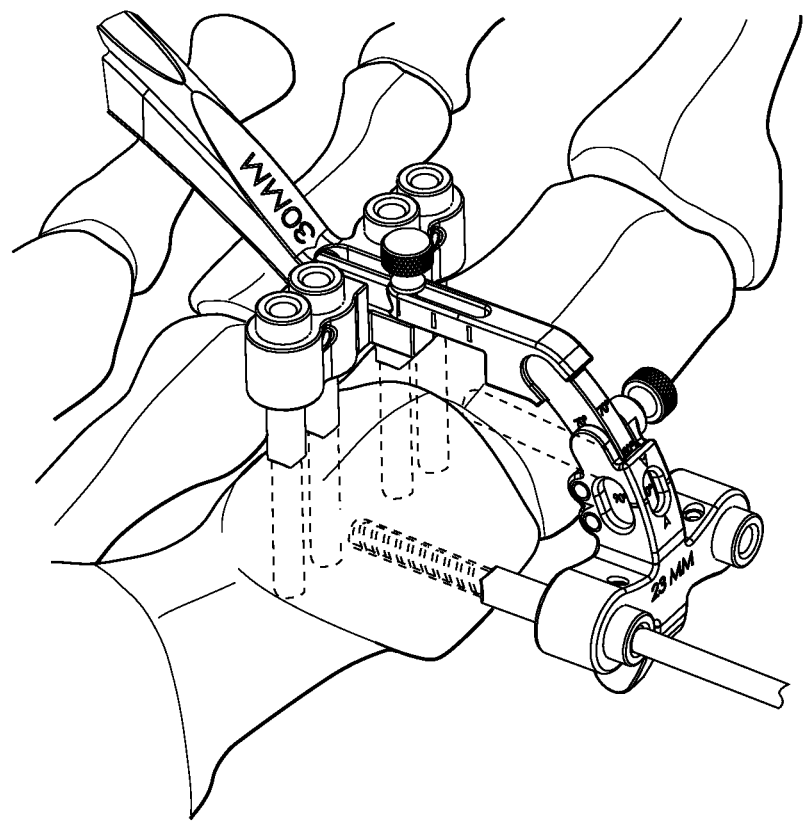
FIG. 11 is perspective view, similar to that of FIG. 10, of an operative portion of the guide tool of FIG. 1 positioned adjacent a bone in after some but not all of the guide holes have been drilled in the bone and before staples are inserted into the guide holes.
Figure 12:
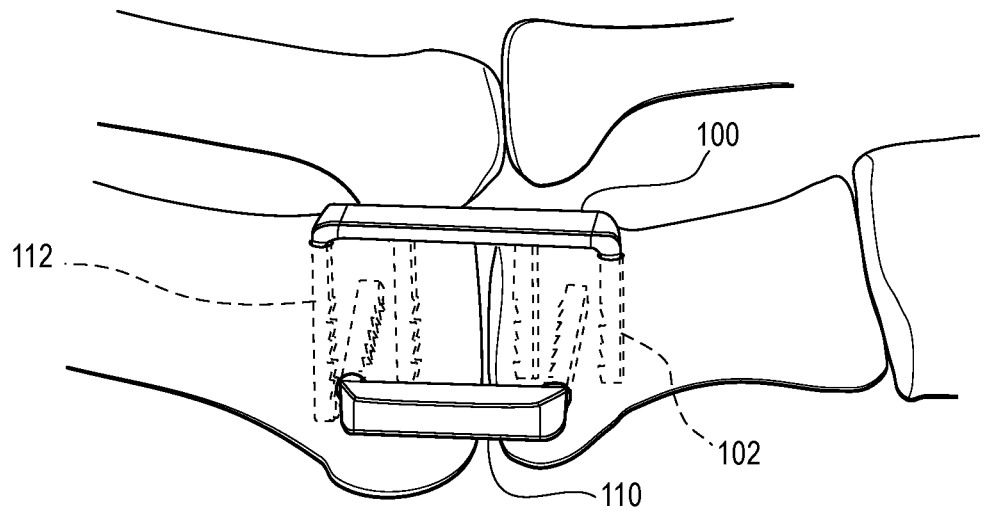
FIG. 12 is a perspective view of a pair of staples having been inserted into holes drilled in the bones.
Figure 20:
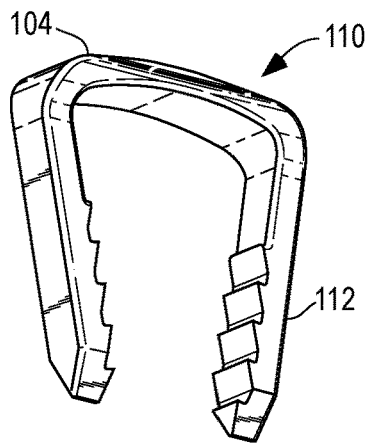
FIG. 20 is a perspective view of a surgical staple having two legs.
Figure 21:
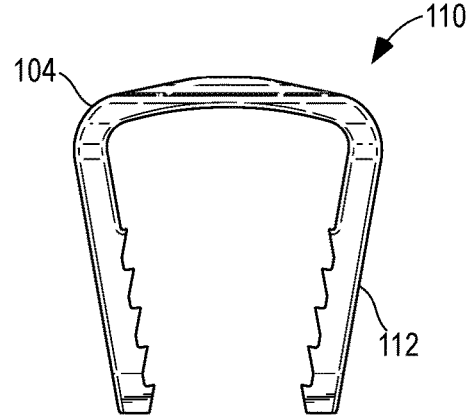
FIG. 21 is a side elevation view of the surgical staple of FIG. 20, showing legs of the staple at acute angles relative to a bridge.
Figure 22:
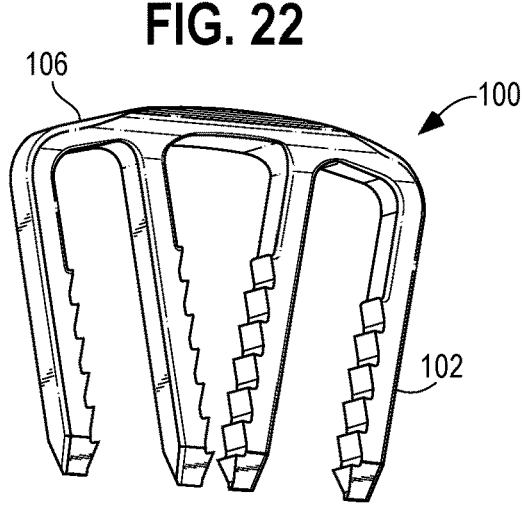
FIG. 22 is a perspective view of a surgical staple having four legs.
Figure 23:
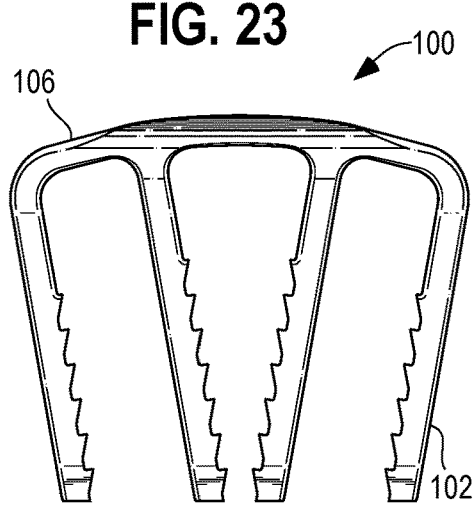
FIG. 23 is a side elevation view of the surgical staple of FIG. 22, showing legs of the staple at acute angle relative to a bridge.

A first embodiment of the guide tool 10 includes a rearward set of drill guides 12 fixed relative to a handle 14 and an adjustable forward set of drill guides 16 that can be selectively fixed relative to the rearward set of drill guides 12, aspects of which are shown in FIGS. 1-12. The guide tool 10 can be used for drilling guide holes in bones for insertion of a legs 102 of a first surgical staple 100 and legs 112 of a second surgical staple 110. The rearward drill guides 12 can be used to drill a plurality of parallel guide holes for receiving the legs 102 of the first staple 100 which, in the exemplary embodiment, has four legs 102 generally in a first staple plane, such as those shown in FIGS. 22-25. The forward drill guides 16 can be used to drill a plurality of parallel holes for receiving the legs of the second staple which, in the exemplary embodiment, has two legs generally in a second staple plane, such as shown in FIGS. 20 and 21. The guide tool 10 is configured such that the holes are aligned so that the first and second staple planes intersect once the staples are inserted into the bones, as shown in FIG. 12.

Broadly, the guide tool 10 includes the handle 14 with an attached rearward set of drill guides 12. An adjustable arm 18 has a linear segment 20 that can be selectively attached to the handle 14 in a variety of different positions. The adjustable arm 18 also has an arcuate segment 22 that is spaced from the handle by the linear segment of the arm. A bracket 24 is slidable along the arcuate segment 22 and carries the forward set of drill guides 16. The bracket, and thus the forward set of drill guides, can be selectively fixed relative to the arcuate segment of the arm.

Each of the drill guides 12, 16 includes a cylindrical sleeve 26 having a through-opening extending along a central axis thereof. In use, a drill bit can be inserted into the through-opening and used to drill a hole. The through-opening and drill bit are preferably sized so that play between the drill bit and the sleeve is minimized so that a hole can be drilled with accuracy. The drill guides also include a separate holder 28 for each of the cylindrical sleeves. Each of the holders includes a through-bore for receiving part of one of the cylindrical sleeves. Each of the cylindrical sleeves can optionally have a serrated edge at the distal tip thereof for seating on an adjacent bone.

The cylindrical sleeves are axially and rotationally secured in the through-bores of the holders. Each of the holders has a pair of aligned apertures tending perpendicular relative to a longitudinal axis passing through a center of the holder. An inner circumferential wall of the holder has partially dished in alignment with the aligned apertures. Each of the cylindrical sleeves also has a dished portion on an outer circumference thereof, extending generally perpendicular relative to the central axis thereof. When one of the cylindrical sleeves is received with the through-bore of one of the holders, the dished portion of the cylindrical sleeve is positioned to face the dished portion of the inner circumferential wall of the holder such that an opening of circular cross-section is formed therebetween. When so arranged, a pin can be positioned with each end being held by the aligned apertures and through the opening formed by the dished portions. The pin is thus fixed to the holder via the aligned apertures thereof. Engagement between the fixed pin and the dished portion of the cylindrical sleeve both prevents rotation of the cylindrical sleeve within the holder and axial movement of the cylindrical sleeve within the holder.

Figure 1:
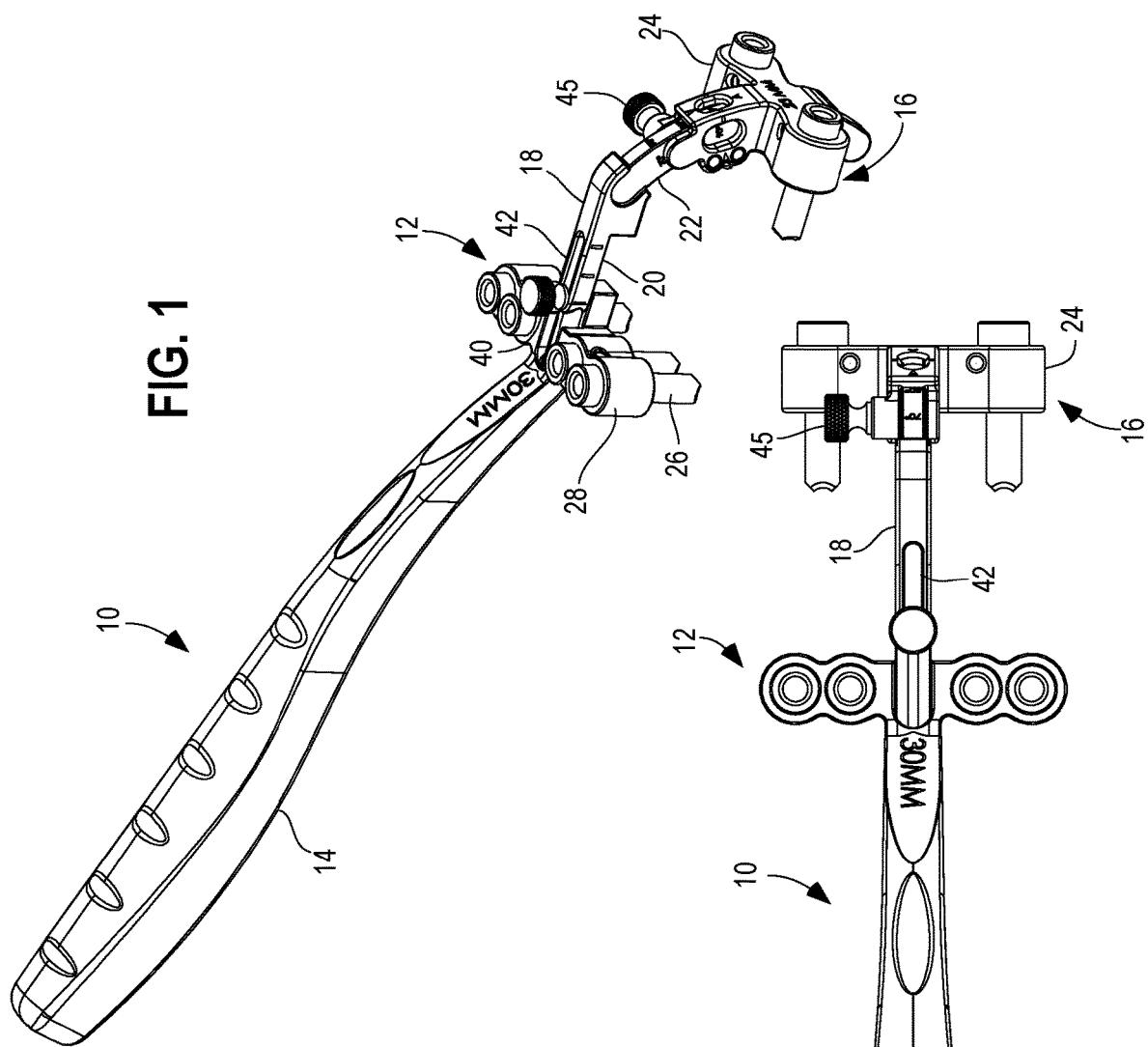
FIG. 1 is a perspective view of an embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple.
Figure 2:
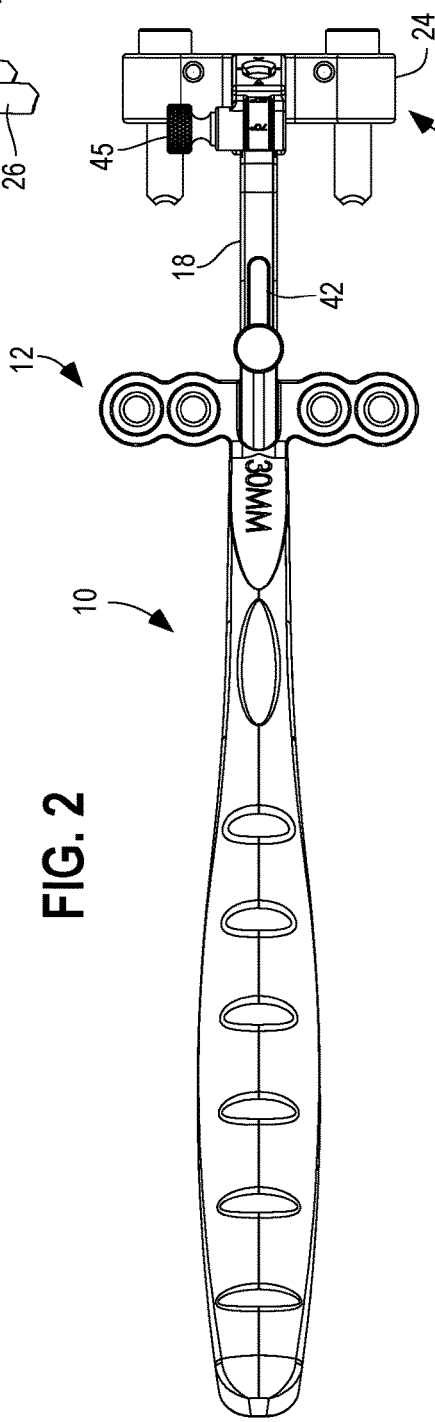
FIG. 2 is a top plan view of the guide tool of FIG. 1.
Figure 3:
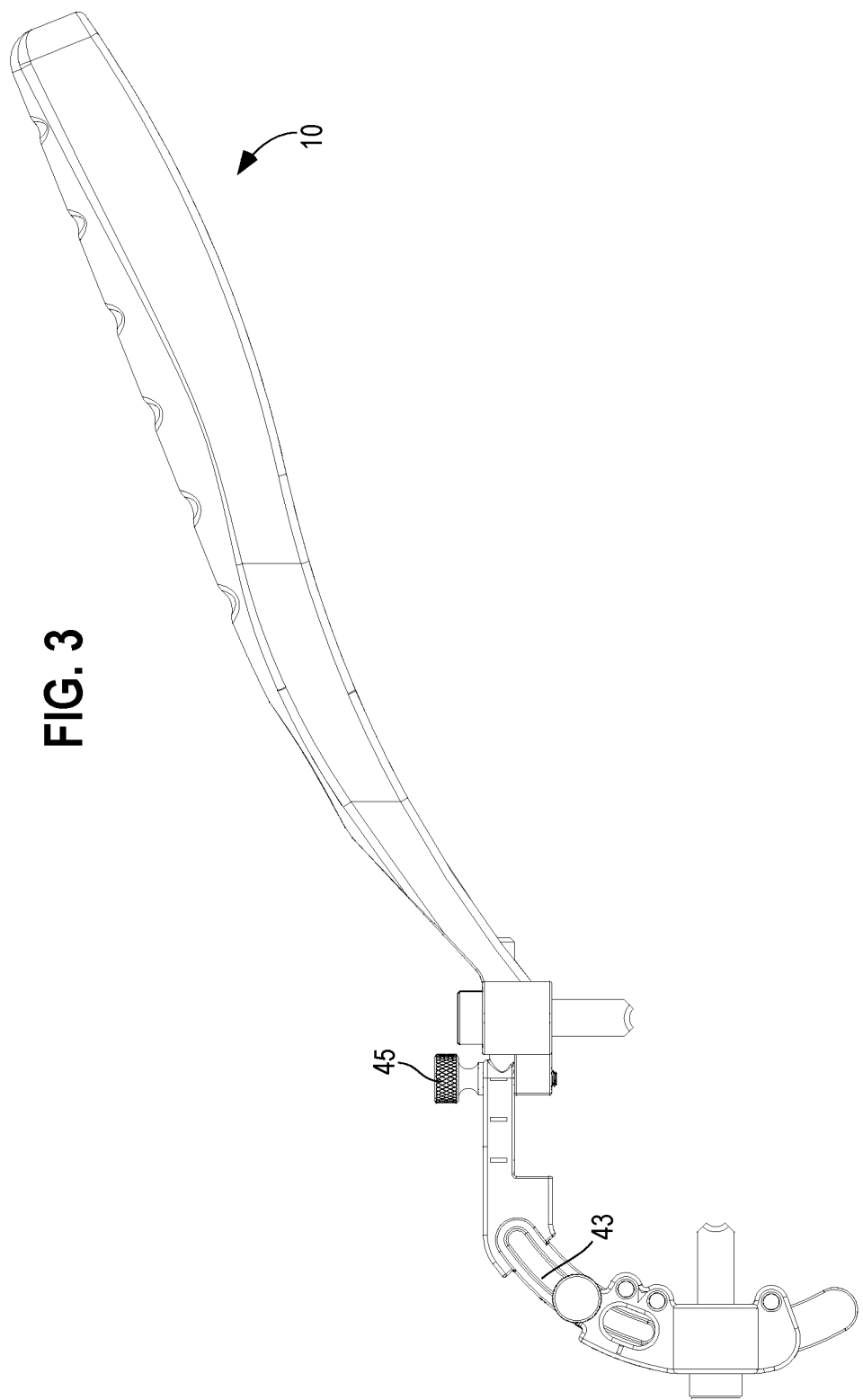
FIG. 3 is a left side elevation view of the guide tool of FIG. 1.
Figure 4:
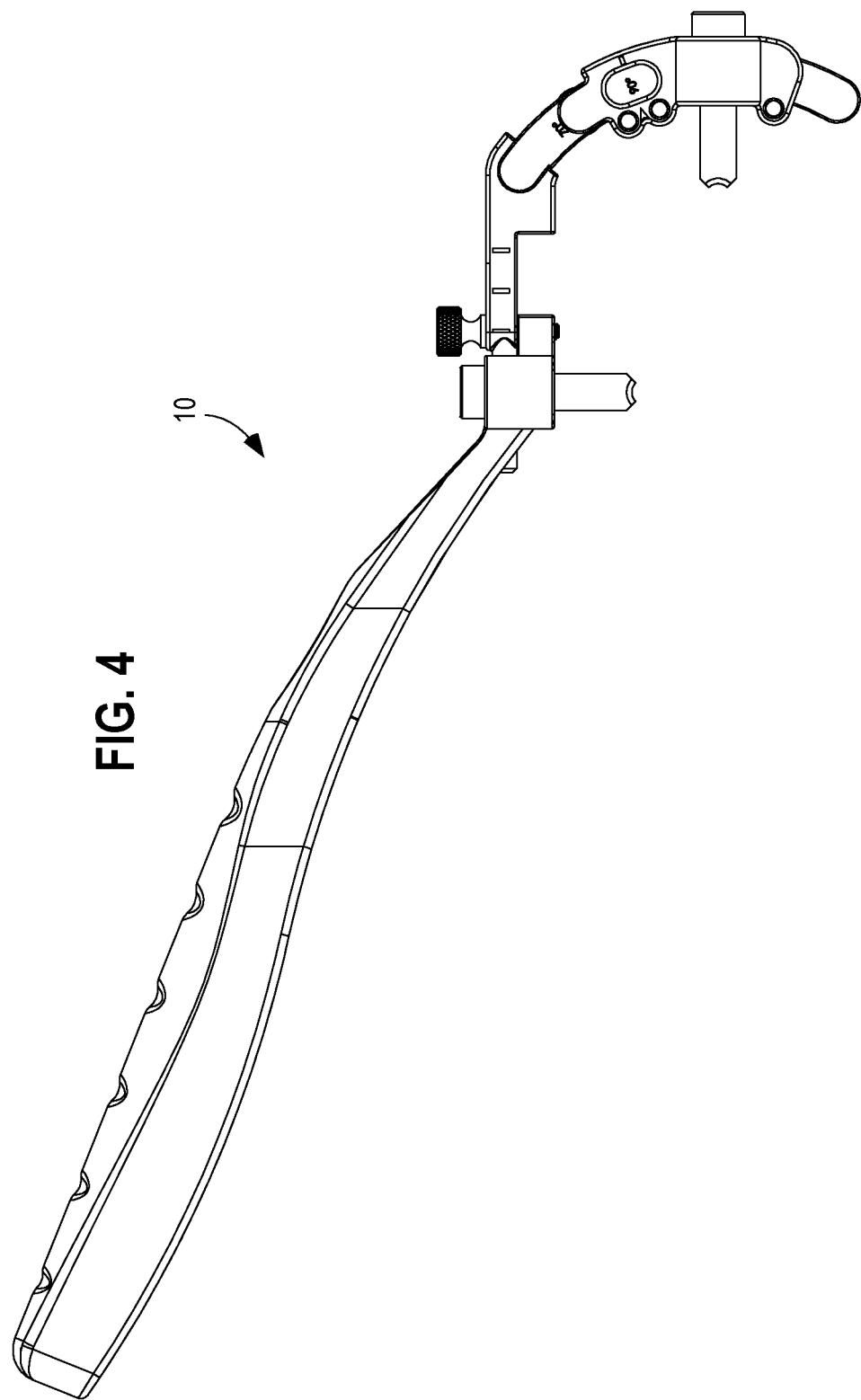
FIG. 4 is a right side elevation view of the guide tool of FIG. 1.
Figure 5:
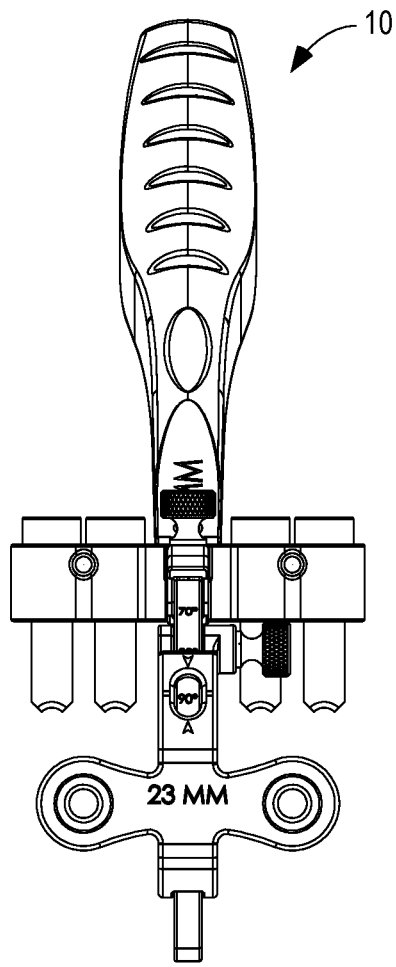
FIG. 5 is a front side elevation view of the guide tool of FIG. 1.

The handle 14 includes a longitudinally extending grasping portion, which can optionally be ergonomically contoured for being held by the hand of a surgeon or other user. As mentioned above, the rearward set of drill guides 12 are attached to the handle 14. More specifically, there are four drill guide holders integrally formed at one end of the handle. The four holders are arranged in a line that is generally perpendicular to the grasping portion of the handle, as shown in FIG. 2. Other arrangements of the holders relative to the handle can be made, e.g., parallel or angled; and the holders do not have to be in a line, but can be in other non-linear arrangements. In the illustrated embodiment, there are four holders. It will be understood that a different number of holders can be used depending upon the number of staple legs to be inserted into holes, e.g., two, three, etc.

Figure 7:
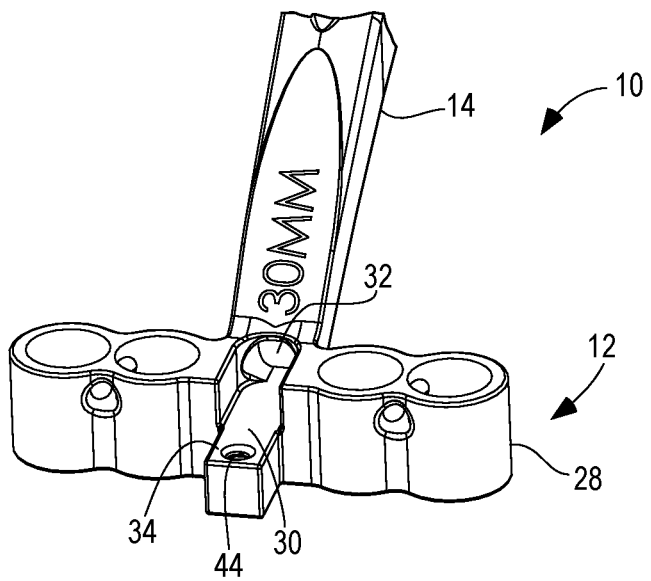
FIG. 7 is a detailed view of the front end of the handle of FIG. 1.
Figure 8:
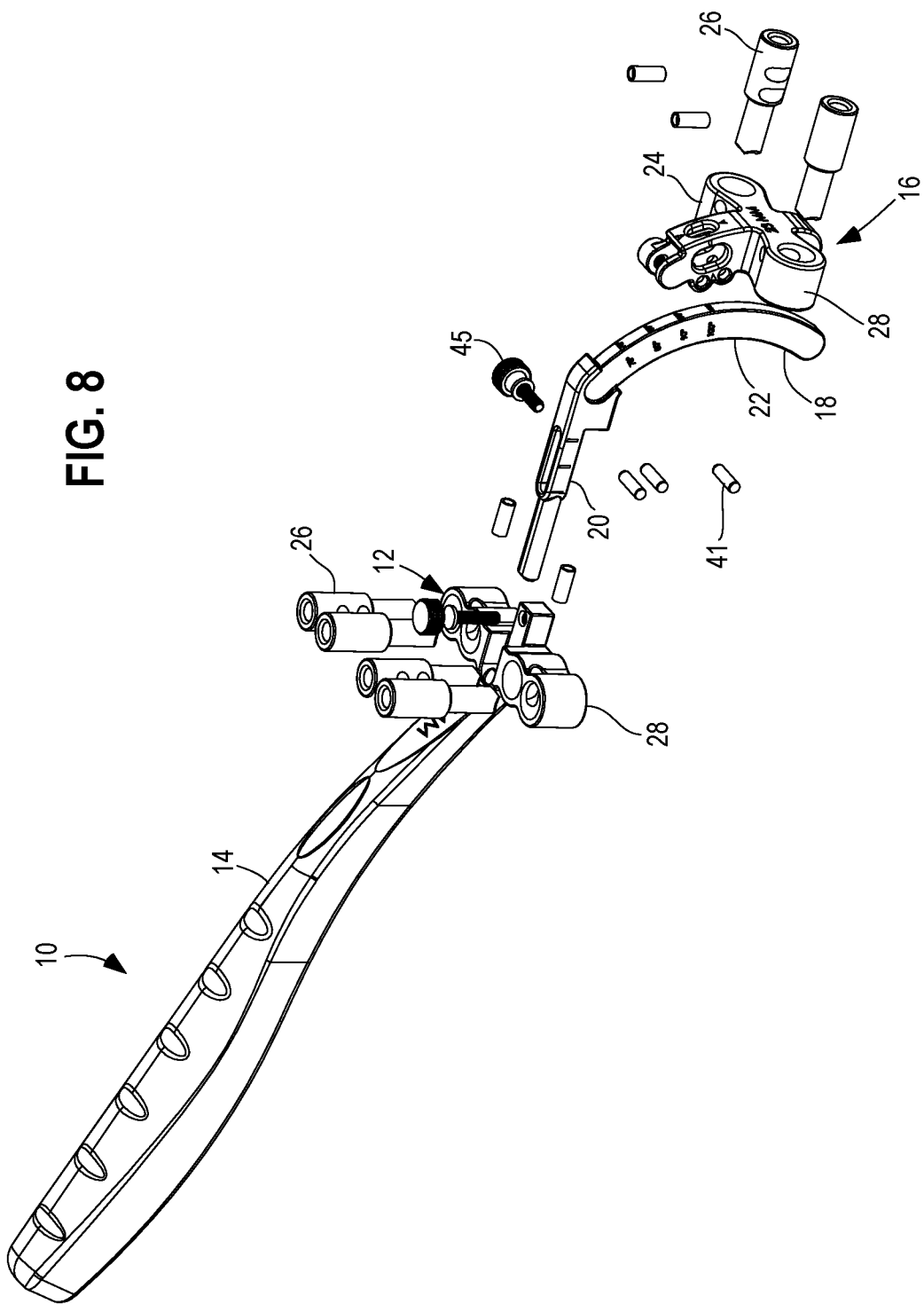
FIG. 8 is an exploded view of the guide tool of FIG. 1.
Figure 9:
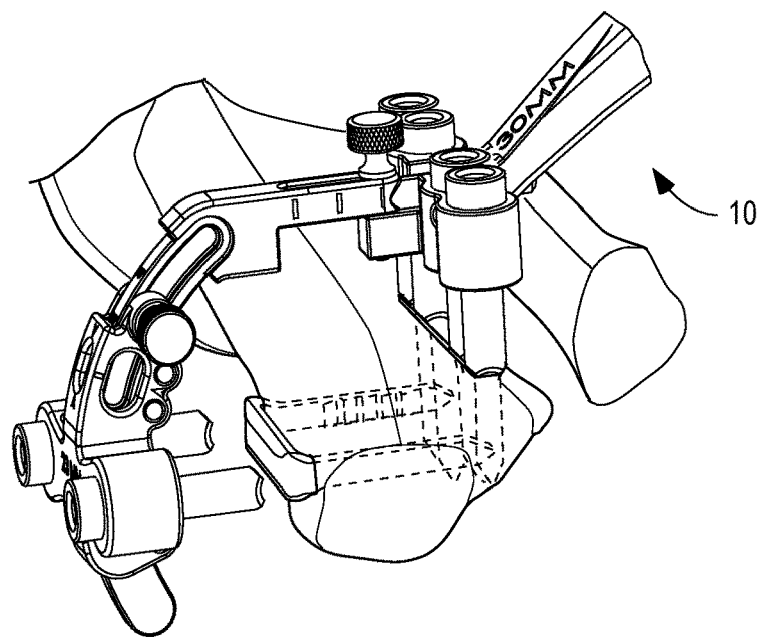
FIG. 9 is a perspective view of an operative portion of the guide tool of FIG. 1 positioned adjacent a bone in after guide holes have been drilled in the bone and staples inserted into the guide holes.

The handle includes an open channel 30 formed between the four holders, as seen in FIG. 7. The channel is configured to receive the linear segment of the adjustable arm. More specifically, two of the holders are on one side of the channel and two of the holders on another side of the channel. The channel has a flat bottom wall, a rear end with an obround opening 32, and a projecting end 34 extending forward of the holders. The linear segment of the adjustable arm terminates in a protuberance that is obround in cross-section and keyed to fit within the oval-shaped opening of the rear end of the channel of the handle. A flattened bottom of the protuberance abuts the flat bottom wall of the channel. Accordingly, engagement between the channel and the protuberance of the linear segment of the arm restricts rotation of the arm relative to the handle.

The arm can be selectively attached relative to the handle, as mentioned above. To that end, a threaded screw or knob 40 can be used to secure the arm to the handle. More specifically, the linear segment of the adjustable arm has an elongated slot 42 formed therein. When the protuberance of the linear segment of the arm is received within the channel of the handle, the slot is positioned above a threaded bore 44 formed in the projecting end of the channel. The knob has a threaded shaft depending from a head with a knurled periphery. The threaded shaft of the knob is inserted through the slot of the linear segment of the arm and into the threaded bore. The tightening of the knob can clamp the arm to the handle. The knob can be removed to either detach the arm from the handle or to loosen to allow the arm to be slidingly adjusted relative to the handle and then tightened.

Figure 6:
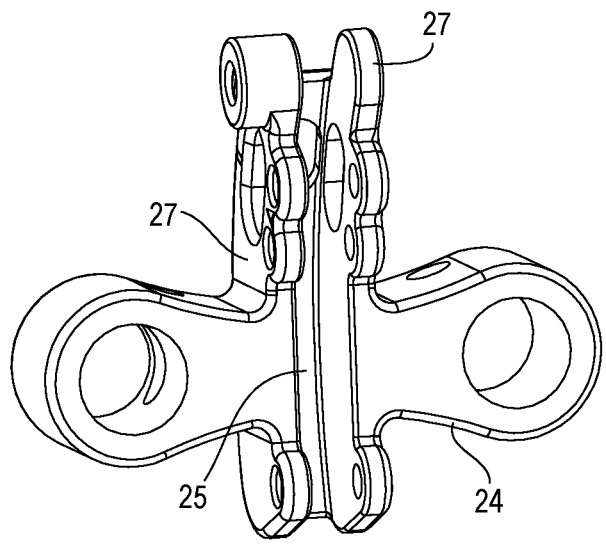
FIG. 6 is a rear perspective view of a movable bracket of the forward guides of the guide tool of FIG. 1.

The bracket 24, which carries the forward set of drill guides, is slidable along the arcuate segment. A pair of the holders are provided on the bracket, one on each side of the arcuate bottom wall thereof. The arcuate segment has an arcuate, radially outward surface and an arcuate, radially inward surface. The arcuate segment has a generally rectangular cross-section. The bracket includes an arcuate bottom wall 25, as shown in FIG. 6, with a pair of lateral, upstanding side walls 27. A radius of curvature of the bottom wall of the bracket generally matches a radius of curvature of the arcuate segment of the arm such that the bottom wall of the bracket can slide along the outward surface of the arcuate segment of the arm. Each of the pair of sidewalls has three apertures. The apertures of one of the pair of sidewalls is aligned with the apertures of the other of the pair of sidewalls. Pins 41 are inserted through aligned apertures, such that there are three pins. The apertures, and thus the pins, are aligned such the dowels can slide along the inward surface of the arcuate segment of the arm. The pins and the arcuate bottom wall sandwich the radially inward surface and the radially outward surface of the arcuate segment, respectively, therebetween.

The pair of sidewalls and the bottom walls optionally have windows formed therein through which indicia on the arcuate segment of the arc can be visible to help with positioning the bracket along the arcuate segment of the arm.

The bracket, and thus the forward set of drill guides, can be selectively fixed relative to the arcuate segment of the arm, as mentioned above. The arcuate segment of the adjustable arm has a generally rectangular cross-section. One side of the arcuate segment has a curved, obround-shaped groove 43. One of the sidewalls of the bracket has an extending ear with a threaded through-bore. A knob 45 is provided to secure the bracket on the arcuate segment of the arm. More specifically, the knob has a threaded shaft depending from a head with a knurled periphery. The threaded shaft of the knob is threaded into the threaded through-bore of the ear of the sidewall of the arcuate segment of the arm and into engagement with a bottom of the groove on the arcuate segment of the arm. The tightening of the knob can clamp the bracket to the arm. The knob can be removed to allow the bracket to be slid off the arm or loosened to allow the bracket to be slidingly adjusted relative to the arm and then tightened to fix the bracket in position relative to the rearward set of drill guides. Ends of the groove on the arcuate segment of the arm can limit the extent to which the bracket can slide on the arm when then threaded shaft is received within the groove but not engaged with the bottom wall thereof.

Turning now to a method of using the first embodiment of the guide tool, the handle can be used to position the rearward set of drill guides against a pair of adjacent bones, as shown in FIG. 10. The adjacent bones can be separate bones or pieces of the same bone and, as used herein, the term bones as used herein is understood to include both two different bones or pieces of the same bone or the same bone even if not into separate pieces. In other words, even if used in the plural sense the term can encompass the singular sense.

The forward set of drill guides can also be positioned against the pair of adjacent bones, also as shown in FIG. 10, with adjustment to the position of the forward set of drill guides being made using the arm and/or the bracket. As used herein, adjacent bones can also include bone pieces of the same bone that require fusion. Optionally, a guide wire for a cannulated screw can be installed in one of the bones. When used, the guide wire can then be threaded through one of the rearward set of drill guides to help with positioning the guide tool adjacent the bones. A first of the holes can then be drilled using a drill bit—attached to a drill—inserted through the first of the holes. A surgeon can drill the remainder of the holes or, optionally, insert one or more removable pins temporarily through the drill guides to temporarily secure the guide tool to the bone or bones. For example, a hole can be drilled into one of the pair of bones using one of the rearward set of drill guides to guide the drill bit; and another hole can be drilled into the same or a different one of the pair of bones using the forward set of drill guides to guide the drill bit, as shown in FIG. 11. Removable pins can be inserted into those holes to temporarily secure the guide tool to the bone or bones. The remainder of the holes can be drilled, after which the pins can be removed and the guide tool removed from adjacent the bones. Staples can then be inserted into the holes that are drilled into the bones to fuse the bones together, as shown in FIG. 12.

Preferably, though not necessarily, the legs of each of the staples in their resting or unbiased state are at acute angles relative to a bridge that joins the legs, as shown in FIGS. 20-25. The staples can optionally be made of a shape memory metal, such as nitinol. The drilled holes made using the rearward set of drill guides are perpendicular to each other, as are the drilled holes made using the forward set of drill guides. The legs of the staples can be temporarily bent to be generally perpendicular relative to the bridges and generally parallel relative to each other and, when in that arrangement, inserted into the holes. An insertion tool, such as that disclosed in U.S. patent application Ser. No. 17/322,580, filed May 17, 2021, which is hereby incorporated herein by reference in its entirety, can engage with the staple to bend and temporarily hold the legs in the perpendicular and parallel arrangement for insertion into the holes. Once the legs are almost completely inserted, the insertion tool can be disengaged from the staple and the staple legs inserted the rest of the way into the holes. Advantageously, the shape memory properties of the staple can cause the legs to want to return to their acutely angled orientation relative to the bridge, thereby compressing the adjacent bones together, preferably with a compressing force that is greater than if the legs in their resting or neutral state were generally perpendicular relative to the bridge.

In a guide tool 210 of a variation of the first embodiment of the guide tool, shown in FIGS. 32-37, a bracket 224, which carries the forward set of drill guides 216, is slidable along an arcuate segment 219 and can be selectively fixed in one of a plurality of different indexed positions. The method of using the variation of the first embodiment can be the same as for the first embodiment, described herein, with the difference being that the forward set of drill guides 216 can be selectively fixed in one of a plurality of different preset, indexed positions. The bracket 224 can include apertures for use with insertion of a guide wire for securing the bracket 224 and, if clamped, the arm 218, relative to the bone or bones.

Figure 35:
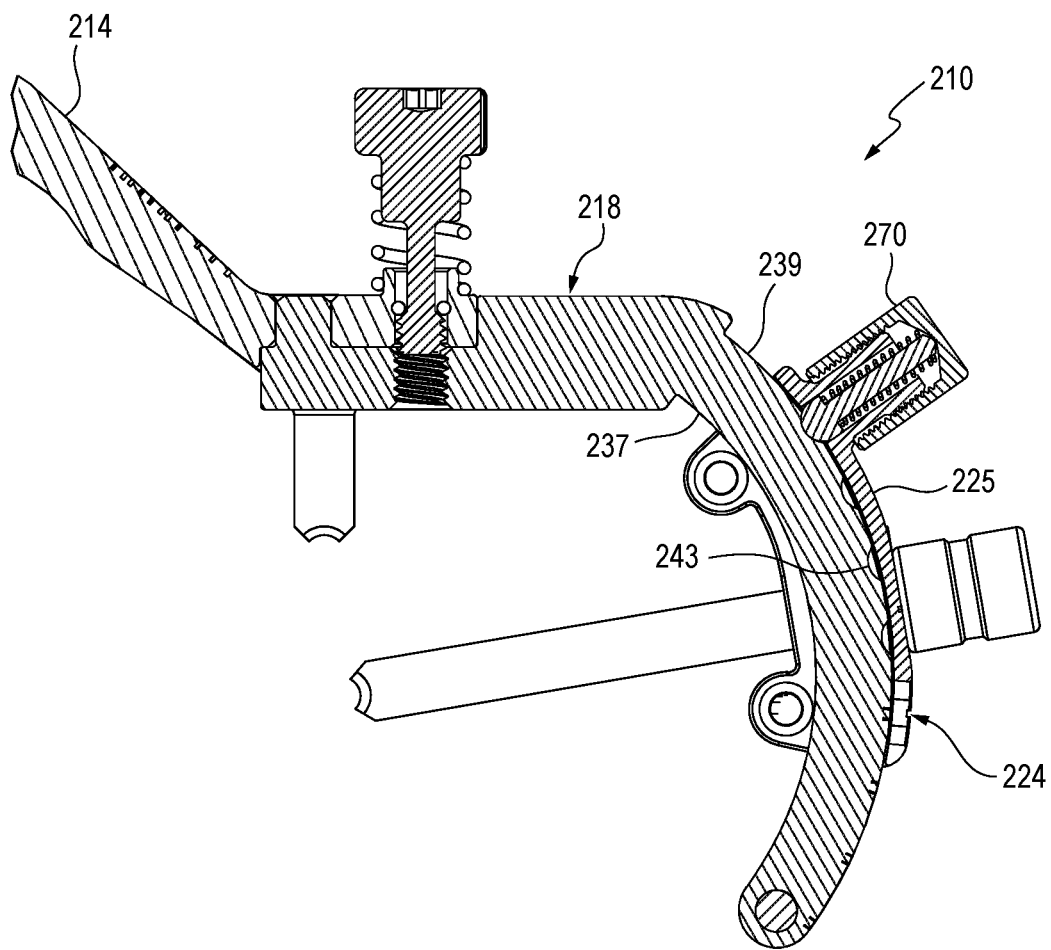
FIG. 35 is a partial section view of the guide tool of FIG. 32 taken along line 35-35 of FIG. 34, showing a bracket in one position and locking knob of the bracket in a first, clamping position.
Figure 36:
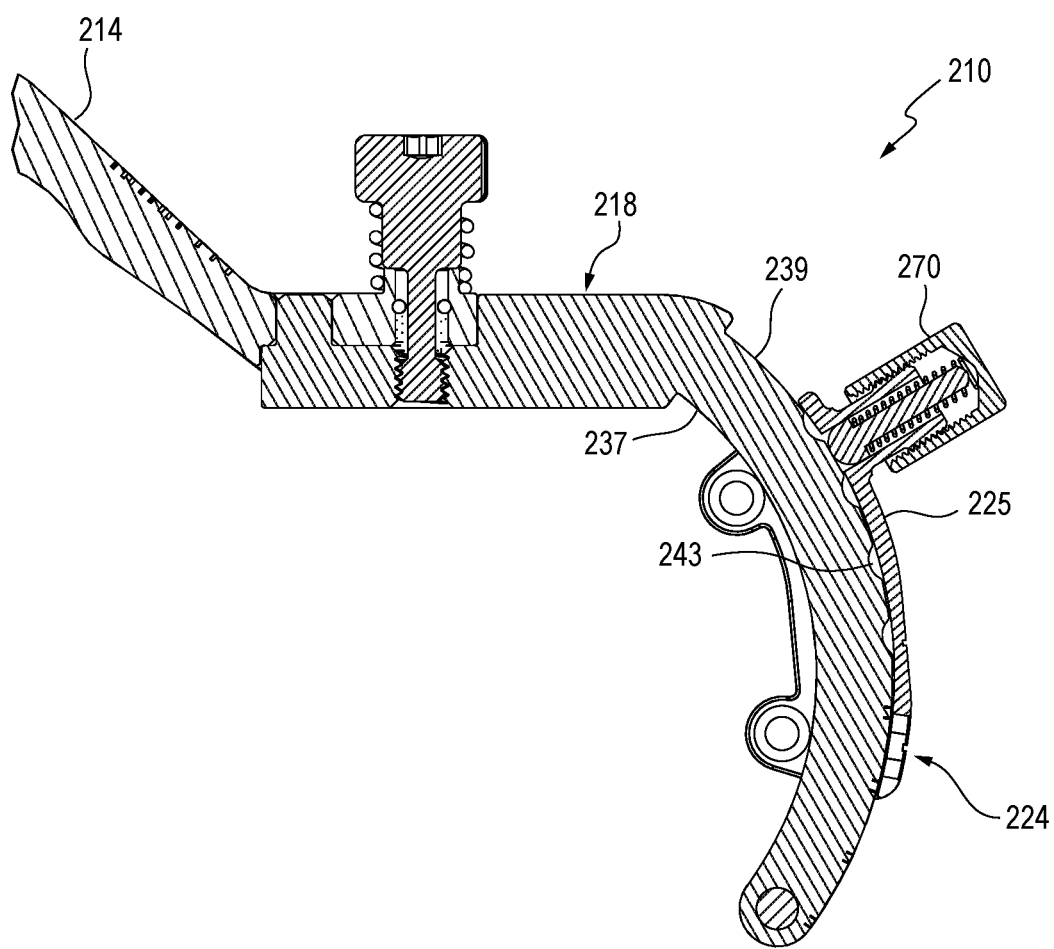
FIG. 36 is a partial section view of the guide tool of FIG. 32, similar to that of FIG. 35 but showing the bracket in a second position and the locking knob of the bracket in a second, unclamping position.
Figure 37:
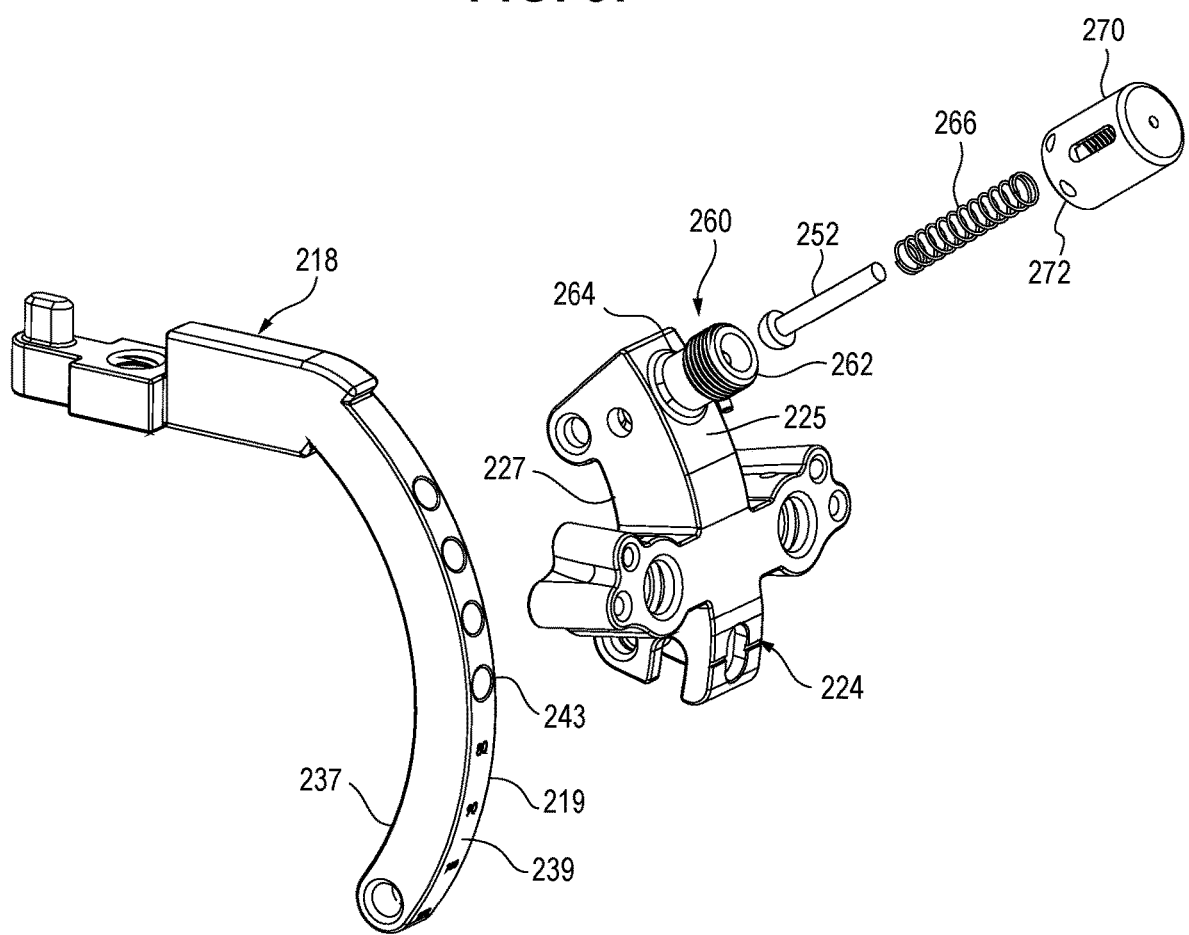
FIG. 37 is an exploded perspective view of the moveable set of forward guides of the tool of FIG. 32.
Figure 38:
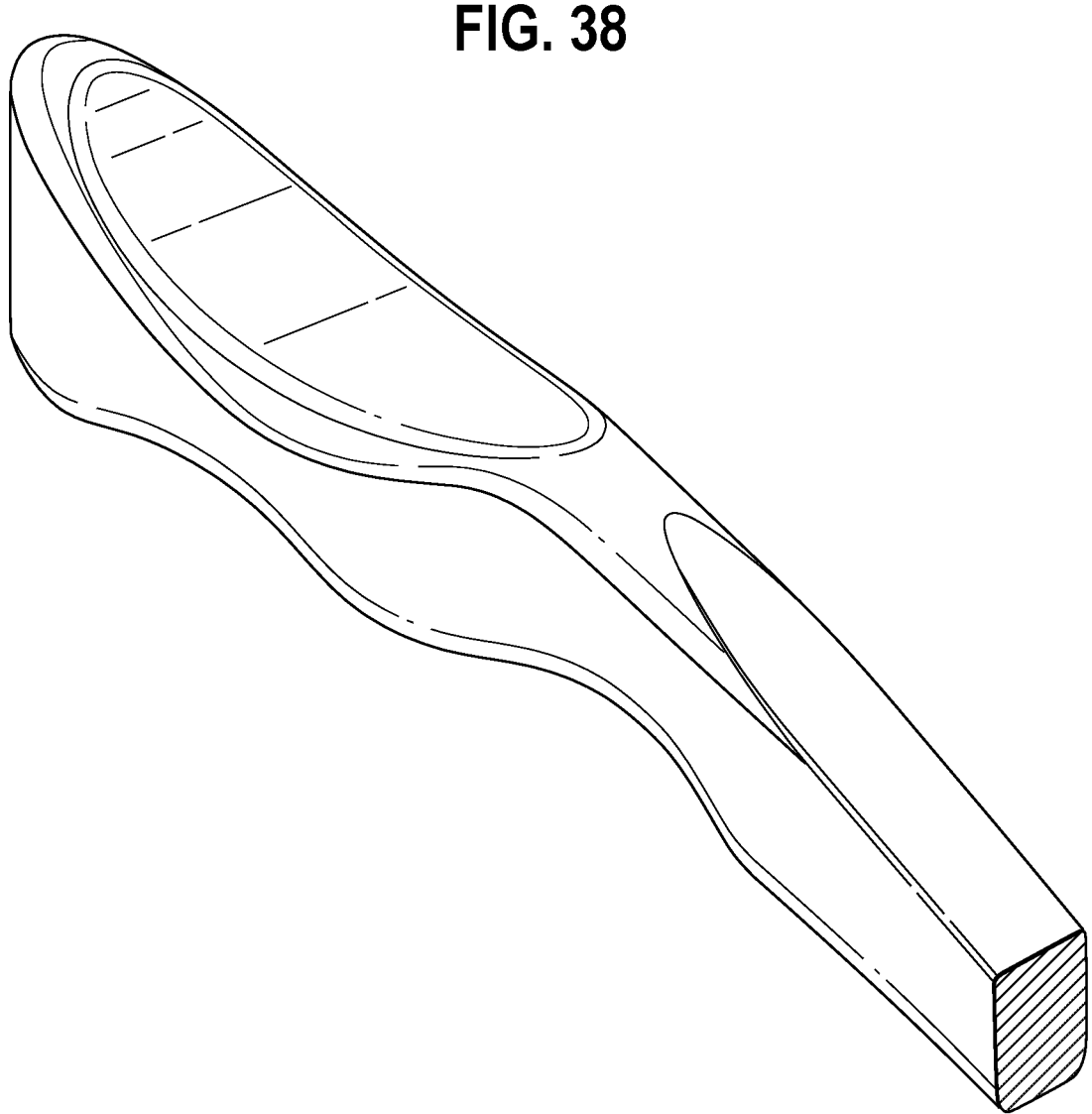
FIG. 38 is a perspective view of a segment of a handle for a surgical tool, with the hatching showing that the handle could be used with any surgical tool.
Figure 39:
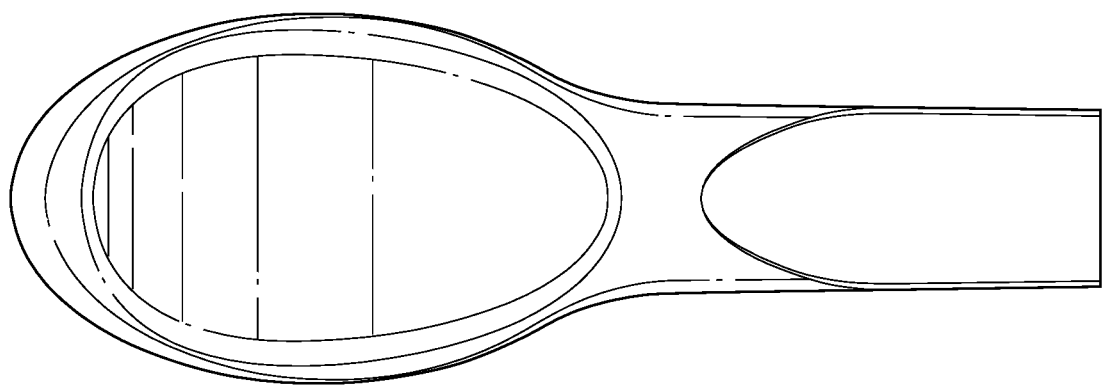
FIG. 39 is a top plan view of the handle of FIG. 38.
Figure 40:
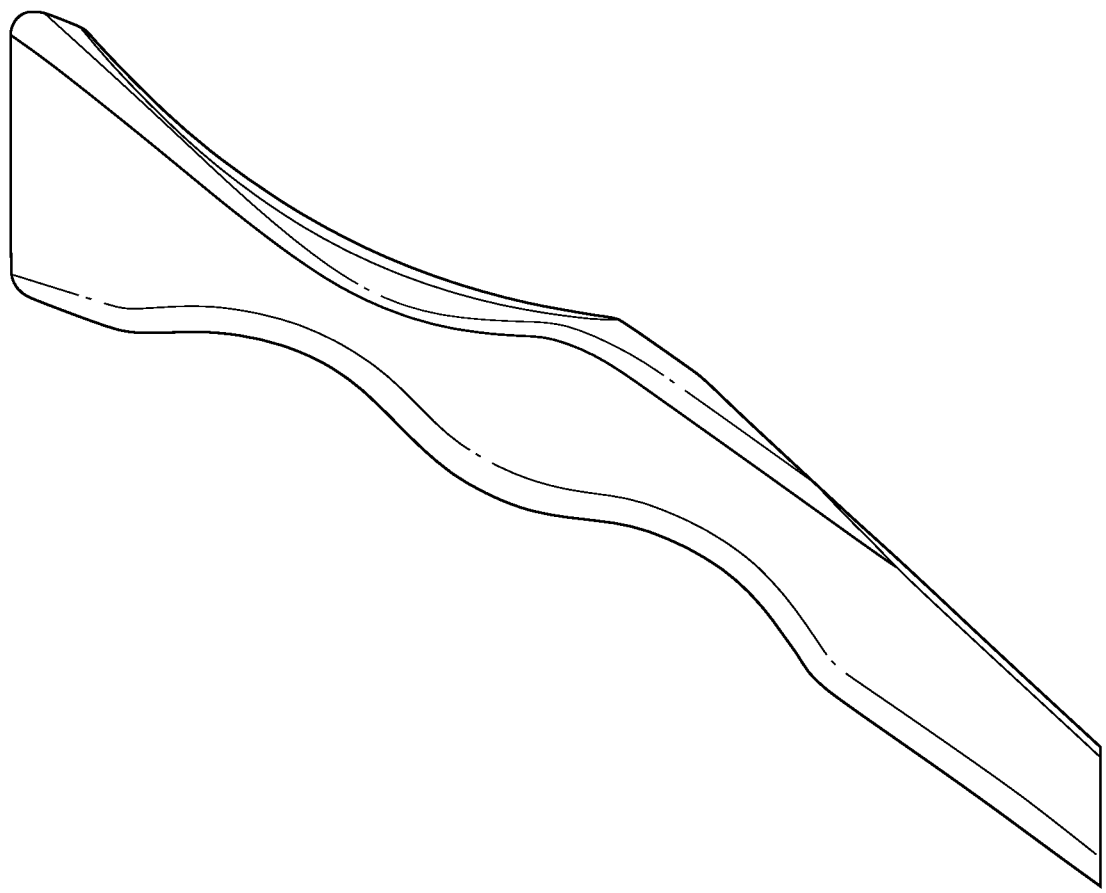
FIG. 40 is a right side elevation view of the handle of FIG. 38, the left side elevation view being the mirror image thereof.
Figure 41:
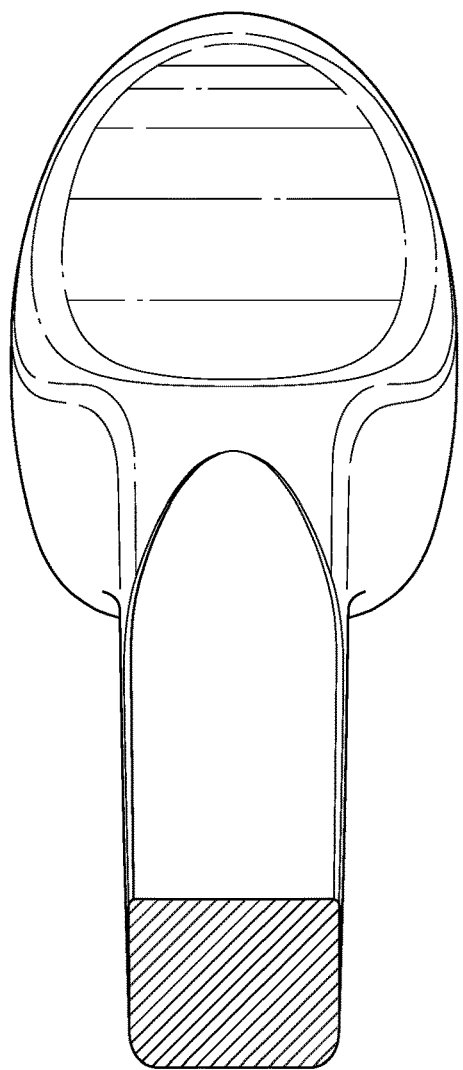
FIG. 41 is a front elevation view of the handle of FIG. 38.
Figure 42:
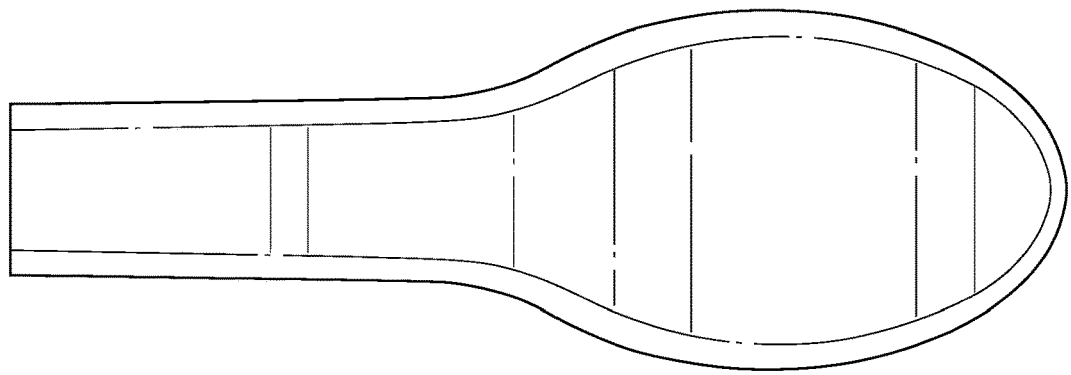
FIG. 42 is a bottom plan view of the handle of FIG. 38.
Figure 43:
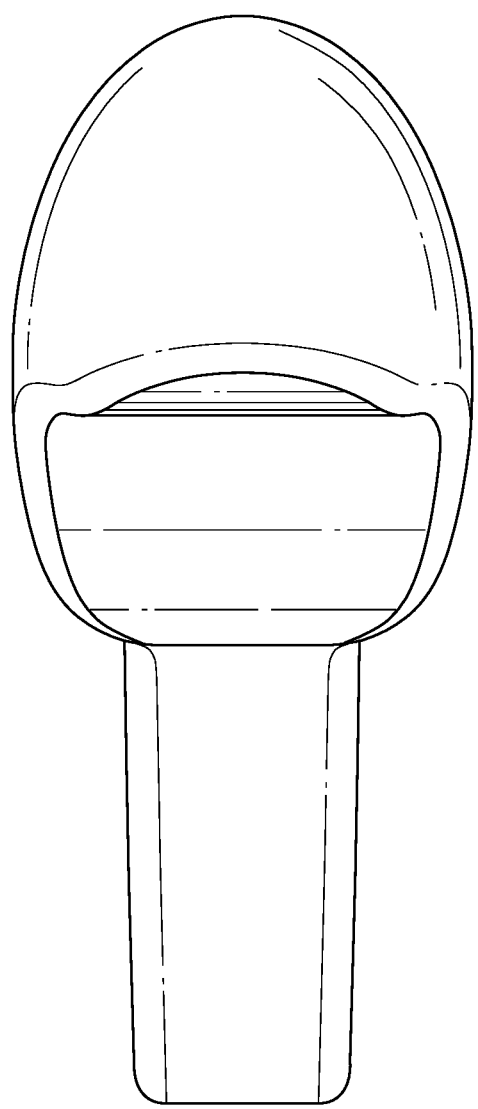
FIG. 43 is a rear elevation view of the handle of FIG. 38.

The bracket 224 of the variation of the first embodiment is otherwise generally similar in construction to the bracket 24 of the first embodiment, with a pair of sidewalls 227 are provided on the bracket 224, one on each side of the arcuate bottom wall thereof. The arcuate segment has an arcuate, radially outward surface and an arcuate, radially inward surface. The arcuate segment has a generally rectangular cross-section. The bracket includes an arcuate bottom wall 225, as shown in FIGS. 35-37, with a pair of lateral, upstanding side walls 227. A radius of curvature of the bottom wall 225 of the bracket 224 generally matches a radius of curvature of the arcuate segment 219 of the arm 218 such that the bottom wall 225 of the bracket 224 can slide along the outward surface of the arcuate segment 219 of the arm 218. Each of the pair of side walls 227 has two apertures. The apertures of one of the pair of side walls 227 is aligned with the apertures of the other of the pair of sidewalls 227. Pins 241 are inserted through aligned apertures, such that there are two pins 241. The apertures, and thus the pins 241, are aligned such the pins 241 can slide along the inward surface, i.e., the underside, of the arcuate segment 219 of the arm 218. The pins 241 and the arcuate bottom wall 225 sandwich the radially inward surface 237 and the radially outward surface 239 of the arcuate segment 219 of the arm 218, respectively, therebetween.

The bracket 224, and thus the forward set of drill guides 216, can be selectively fixed relative to the arcuate segment of the arm, as mentioned above, in one of a plurality of preset indexed positions. The arcuate segment 219 of the adjustable arm 218 has a plurality of detents 243 on the radially outward surface 239 thereof, as shown in FIGS. 35-37. The bracket 224 carries a locking pin 252 that can be partially received in one of the plurality of detents 243 and locked or fixed so that the bracket 224, and thus the forward set of drill guides 216, is fixed in one of a plurality of present positions along the arm 218.

More specifically, the arcuate bottom wall 225 of the bracket 224 has an upstanding stem 260, shown in FIGS. 35-37, with a central opening extending through the stem 260 and the bottom wall 225 of the bracket 224. The locking pin 252 is slidably received with the central opening of the stem 260. One end of the locking pin 252 is positioned to be received in one of the plurality of detents 243, as shown in FIG. 35. The other end of the locking pin 252 extends through the central opening of the stem 260.

A knurled locking knob 270 is attached to the stem 260 and has two positions, as will be explained further herein. The knurled locking knob 270 has an inner bore for receiving a second end portion of the locking pin 252. The inner bore also has an inner thread that can threadingly engage an outer thread 262 of the upstanding stem of the bracket 224. A spring 266 surrounds the second end portion of the locking pin 252 and biases the locking pin 252 into engagement with one of the plurality of detents 243 of the arm 218. The locking knob 270 can be rotated clockwise or counterclockwise to axially move the knob 270 along the stem 260 either away from the bottom wall 225 of the bracket 224, with counterclockwise rotation, or toward the bottom wall 225 of the bracket 224, with clockwise rotation.

In a first, clamping position, shown in FIG. 35, the locking knob 270 is rotated clockwise until the locking pin 252 is clamped between the locking knob 270 and the arm 218, thereby fixing the bracket 224—and thus the forward set of drill guides 216—relative to the arm 216. In a second position, shown in FIG. 36, the locking knob 270 is rotated counterclockwise until the locking pin 252 is no longer clamped and the bracket 224 can slide along the arm 218. When in the second position, the spring 266 biases the locking pin 252 away from the arm 218. However, as the bracket 224 slides along the arm 218, the locking pin 252 can axially move within the inner bore of the locking knob 270. When sliding along the arm 218, when the one end of the pin 252 engages with one of the detents 243 a small force from the spring 266 is required to move the one end of the pin 252 out of engagement with the one of the detents 243. A user can feel that a force is required to slide the bracket 224 further once the pin 252 has engaged with the one of the detents 243, thereby providing tactile feedback that one of a plurality of indexed positions of the bracket 224 along the arm 218 has been reached. The plurality of preset positions can be selected according to the particular needs of the guide tool 210, and can, for example, be at various angles along the arm 218 of between 30 and 150 degrees, for example, 30, 45, 60, 75, 90, 105, 120, 135 and 150 degrees, or other increments therebetween, e.g. increments of 5, 7.5, 10, etc. degrees.

The axial position of the locking knob 270 relative to the stem 260 of the bracket 224 when in the second position is limited. More specifically, the stem 260 includes an annular groove 264 positioned between the outer thread 262 and the bottom wall 225 of the bracket 224. The locking knob 270 includes a locking bore 272 passing through the central bore but offset relative to a central axes of the central bore. A fixation pin 274 can be received with the locking bore 272 of the locking knob 270. The fixation pin 274 is positioned such that the it can axially move up and down within the annular groove 264 when the locking knob 270 is rotated to move between the first and second position, and vice versa, However, when the fixation pin 274 reaches an upper limit of the groove 264, at the intersection with the outer threads 262, further counterclockwise rotation of the locking knob 270 is prevented by engagement of the fixation pin 274 with the intersection with the outer threads 262 where there is a larger diameter compared to that of the annular groove 264.

The arm 218 includes an upper stop, in the form of a step in the arm 218, and a lower stop, in the form of a pin received in an aperture of the arm 218, as shown in FIGS. 32, 33, 35 and 36. The upper and lower stops limit the extend to which the bracket 224 can slide along the arm 218.

Figure 26:
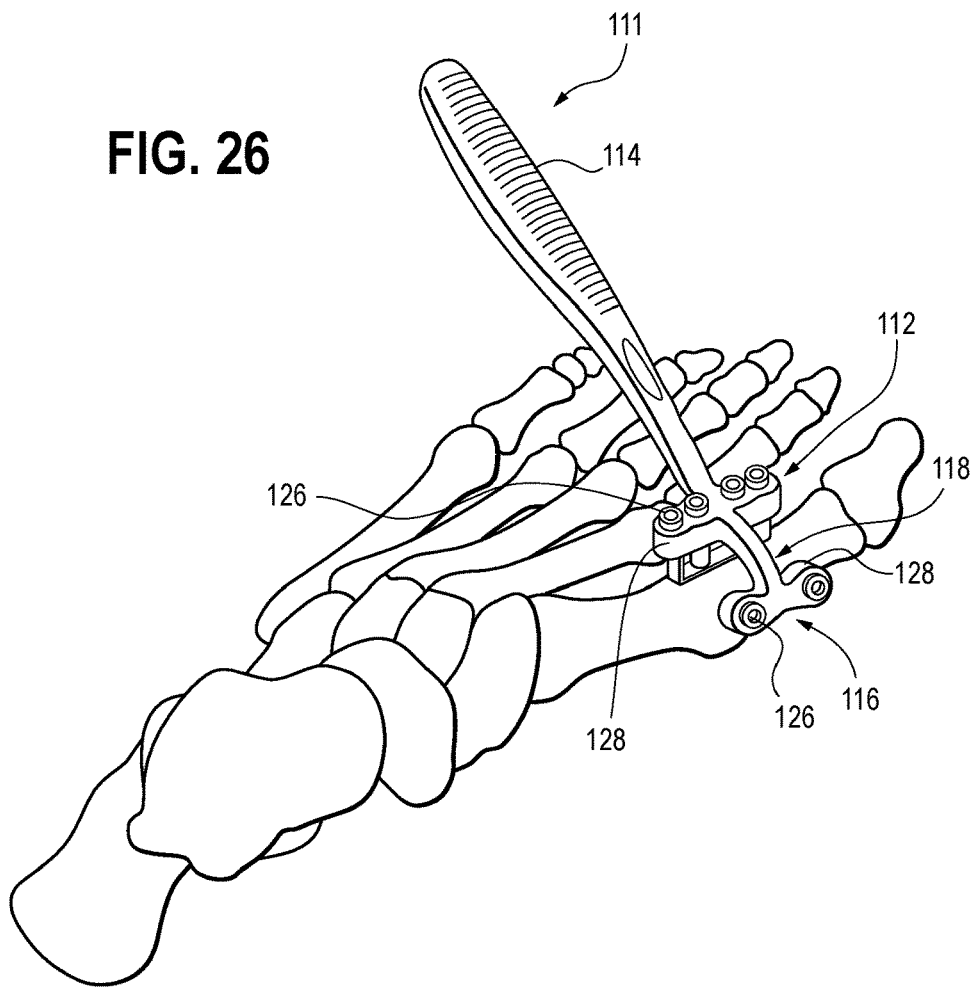
FIG. 26 is a perspective view of yet an alternative embodiment of a guide tool for use in drilling holes in bones for insertion of a first surgical staple and a second surgical staple, the guide tool having a set of rearward guides for use in drilling holes to receive legs of the first surgical staple and a fixed set of forward guides for use in drilling holes to receive legs of the second surgical staple.
Figure 27:
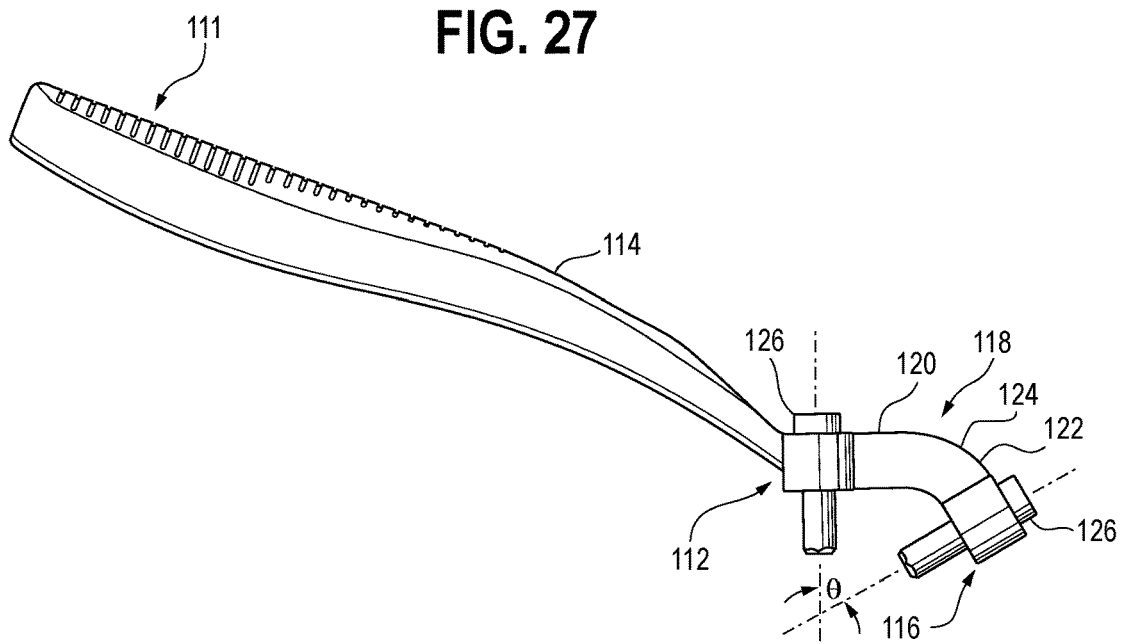
FIG. 27 is a side elevation view of the guide tool of FIG. 26.

Another variation of the first embodiment of the guide tool is depicted in FIGS. 26 and 27, with like numbers referencing like parts. The guide tool 111 depicted in FIGS. 26 and 27 includes a rearward set of drill guides 112 fixed relative to a handle 114 and a forward set of drill guides 116. This variation differs from those of FIGS. 1-12 and 32-36 in that the forward set of drill guides 116 is fixed. The fixation is permanent, i.e., the forward set of drill guides 116 cannot be adjusted relative to the rearward set of drill guides 112. Optionally, the rearward set of drill guides 112 and the forward set of drill guides 116 are formed of a unitary body. The handle 114 can also be unitary with the guides 112, 116, or separately attached.

As with the first embodiment and the variation described above, the guide tool 111 of FIGS. 26 and 27 can be used for drilling guide holes in bones for insertion of a legs 102 of a first surgical staple 100 and legs 112 of a second surgical staple 110. The rearward drill guides 112 can be used to drill a plurality of parallel guide holes for receiving the legs 102 of the first staple 100 which, in the exemplary embedment, has four legs 102 generally in a first staple plane, such as those shown in FIGS. 22-25. The forward drill guides 116 can be used to drill a plurality of parallel holes for receiving the legs of the second staple which, in the exemplary embodiment, has two legs generally in a second staple plane, such as shown in FIGS. 20 and 21. The guide tool 111 is configured such that the holes are aligned so that the first and second staple planes intersect once the staples are inserted into the bones, as shown in FIG. 12.

The guide tool 111 includes the handle 114 with the permanently attached rearward set of drill guides 112. A forward-extending arm 118 has a first segment 120 and a second segment 122 with a bend 124 therebetween. The forward set of drill guides 116 and the rearward set of drill guides 112 can be positioned such holes made with one set are at a fixed angle relative to the holes made with the other set. This can translate into the first and second staple plates intersecting at a generally corresponding fixed angle. The fixed angle can be, for example, between 30 and 150 degrees, for example, 30, 45, 60, 75, 90, 105, 120, 135 and 150 degrees, or other increments therebetween, e.g. increments of 5, 7.5, 10, etc. degrees. Although an angle of approximately 60 degrees is shown, it will be understood that the tool 111 can be constructed to result in a different angle. For example, a projection 113 along one of the central axes of the guides of the rearward set of drill guides 112 can be considered to intersect a projection 115 along one of the central axes of the forward set of drill guides 116 when viewed laterally, i.e., is a side elevation view as shown in FIG. 27, although the projections do not actually intersect when viewed from above, e.g., FIG. 26. The intersection between the two projections 113, 115 can have an inside angle θ, as shown in FIG. 27. The angle ⊖ can be of any suitable angle, such as, for example, between 30 and 150 degrees, for example, 30, 45, 60, 75, 90, 105, 120, 135 and 150 degrees, or other increments therebetween, e.g. increments of 5, 7.5, 10, etc. degrees, while an angle of about 60 degrees is shown in FIG. 27.

Each of the drill guides 112, 116 includes a cylindrical sleeve 126 having a through-opening extending along a central axis thereof. As described in connection with the prior embodiments, in use, a drill bit can be inserted into the through-opening and used to drill a hole. The through-opening and drill bit are preferably sized so that play between the drill bit and the sleeve is minimized so that a hole can be drilled with accuracy. The drill guides also include a separate holder 128 for each of the cylindrical sleeves. Each of the holders 128 includes a through-bore for receiving part of one of the cylindrical sleeves 126. Each of the cylindrical sleeves 126 can optionally have a serrated edge at the distal tip thereof for seating on an adjacent bone.

The cylindrical sleeves 126 are optionally axially and rotationally secured in the through-bores of the holders 128, as described above.

The handle 114 includes a longitudinally extending grasping portion, which can optionally be ergonomically contoured for being held by the hand of a surgeon or other user. As mentioned above, the rearward set of drill guides 112 are fixed relative to the handle 114. More specifically, there are four drill guide holders integrally formed at an end of the handle. There are also four drill guides of the forward set of guides 116. The holders of each of the respective sets are arranged such that central axes thereof each lie in a common plane, which planes are generally perpendicular to the grasping portion of the handle. Other arrangements of the holders can be made, e.g., parallel or angled; and the holders do not have to be in a line, but can be in other non-linear arrangements. In the illustrated embodiment, there are four holders 128 of the rearward array 112 and two holders 128 of the forward array 116. A different number of holders can be used depending upon the number of staple legs to be inserted into holes, e.g., two, three, etc.

The methods of using the variation of FIGS. 26 and 27 can be the same as those of FIGS. 1-12 and 31-36, with the difference being that the forward set of drill guides 116 are fixed relative to the reward set of drill guides 112. Moreover, as shown, the forward set of drill guides 116 and the rearward set of drill guides 112, and, specifically, the holders thereof, are formed of a unitary body. The unitary body can also include the handle 114. The unitary body can be cast, injection molded, machined or otherwise manufactured using a suitable techniques, including being permanently joined together, e.g., welding, fastened, or the like.

Figure 13:
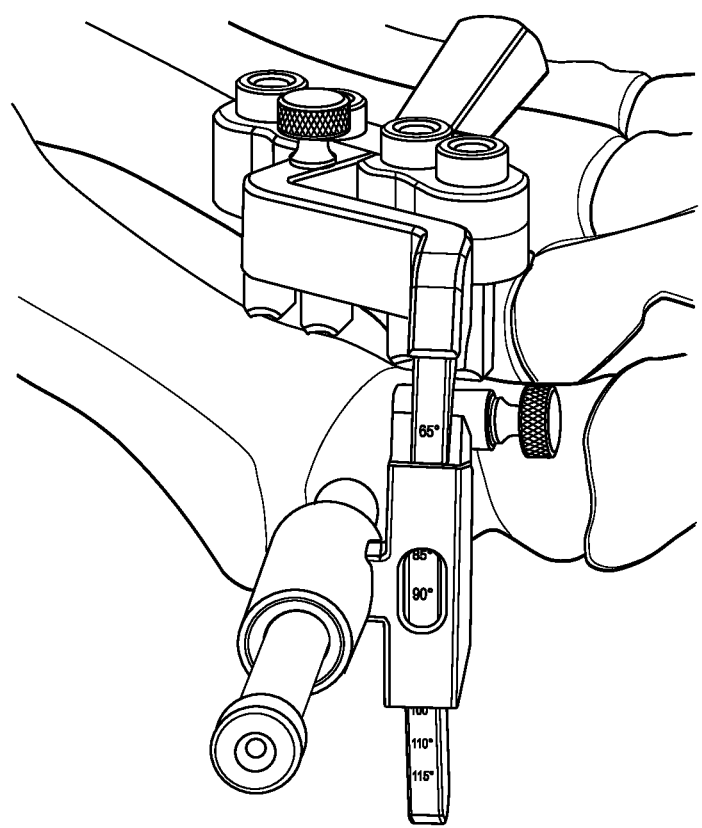
FIG. 13 is a perspective view of a second embodiment of a guide tool for use in drilling holes in bones for insertion of a surgical staple and a bone screw, the guide tool having a set of rearward guides for use in drilling holes to receive legs of the surgical staple and a moveable forward guide for use in drilling a hole to receive the bone screw, the guide tool being positioned adjacent bones for drilling holes.
Figure 14:
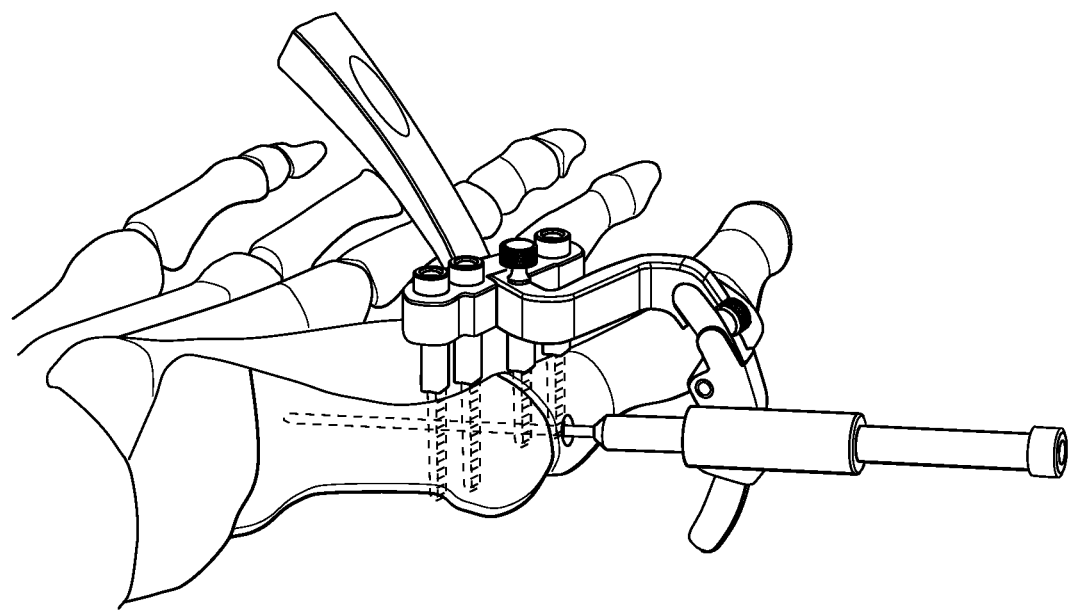
FIG. 14 is a different perspective view of the tool of FIG. 13 positioned adjacent bones for drilling holes, showing a guide wire inserted through a pin disposed in the forward guide.
Figure 15:
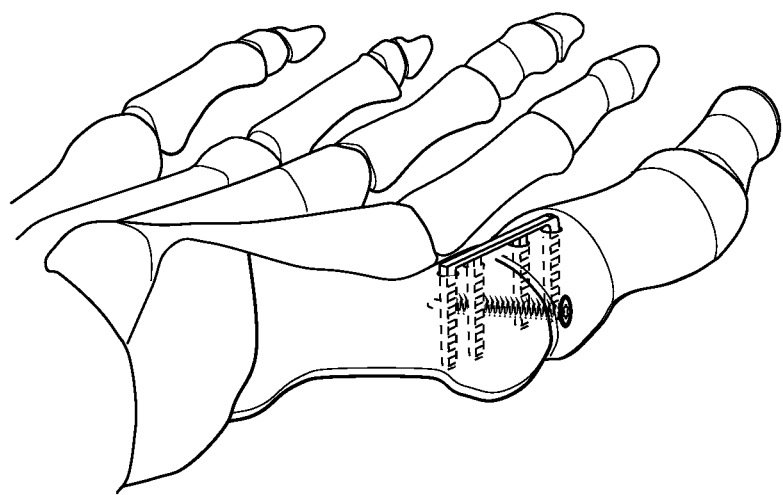
FIG. 15 is a perspective view of a staple and a screw having been inserted into holes drilled in the bones.

A second embodiment of the guide tool is shown in use in FIGS. 13 and 14, with like parts having like numbers as compared with the first embodiment of the guide tool. The second embodiment of the guide tool differs from that of the first embodiment in that instead of being used to drill holes for a first staple and a second staple, the guide tool is configured to drill holes for only the legs of one staple and another hole for a bone screw. In particular, the forward set of drill guides is replaced by a single drill guide. Because a bone screw is used instead of one of the staples, the bone screw must be inserted such that it spans between both bones; thus, the hole drilled for the bone screw must also span between both bones. This is accomplished by the length of the bone screw as well as the angle in which the bone screw is inserted. The forward drill guide is angled such that the drill bit drills a hole that is angled, i.e., not perpendicular, to a plane of the holes for the legs of the staple. The linear and arcuate segments of the adjustable arm are at an obtuse angle relative to each other, as shown in FIGS. 13 and 14, such that a hole drilled using the forward drill guide will is angled to a plate of the holes for the legs of the staple. Like the first embodiment, a guide wire can optionally be used for aligning the guide tool of the second embodiment with the bone or bones. The holes can be sequentially drilled using the drill guides and, optionally, one or more pins can be used for temporarily securing the guide tool to the bone or bones. After drilling of the guide holes, the staple and the screw can be inserted, as shown in FIG. 15.

Figure 28:
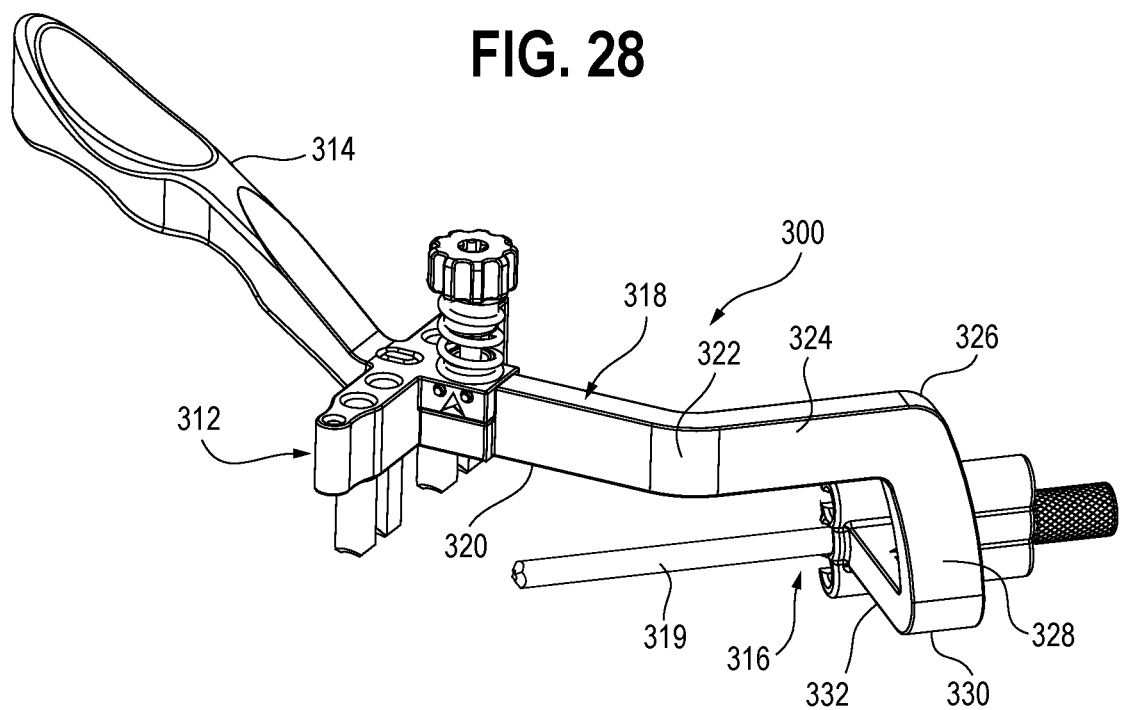
FIG. 28 is a perspective view of another alternative embodiment of a guide tool for use in drilling holes in bones for insertion of a surgical staple and a bone screw, the guide tool having a rearward set of guides for use in drilling holes to receive legs of the surgical staple and a set for forward guides for use in drilling a hole to receive the bone screw.
Figure 29:
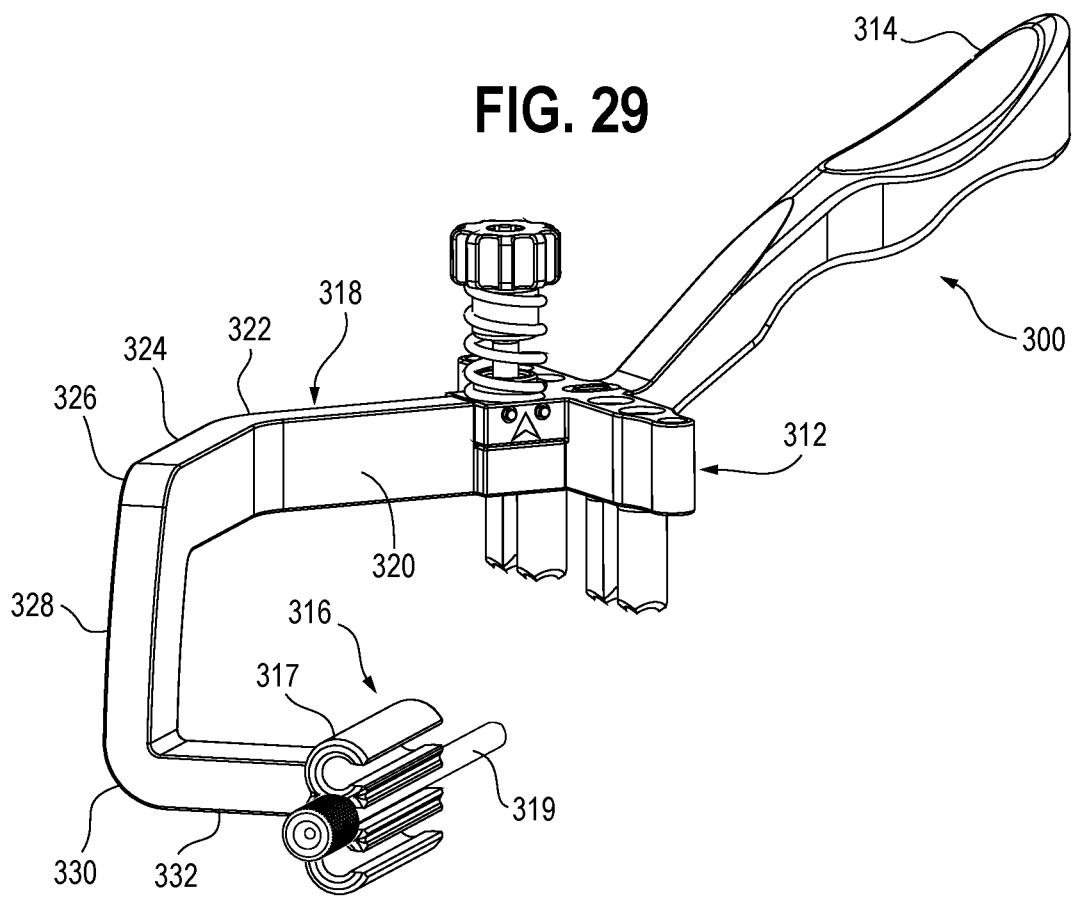
FIG. 29 is a different perspective view of the guide tool of FIG. 28.
Figure 30:
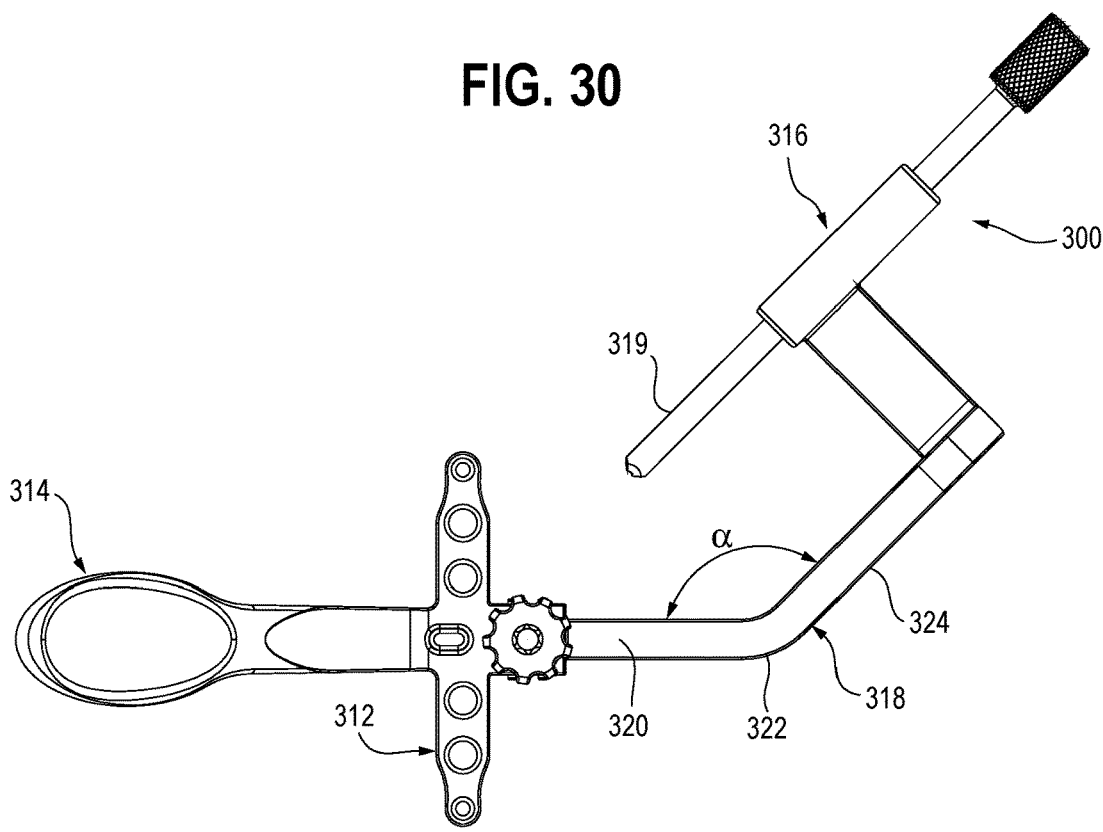
FIG. 30 is a top plan view of the guide tool of FIG. 28.

A first variation of the second embodiment of the guide tool is shown in FIGS. 28-30. Like the second embodiment of the guide tool, the guide tool 300 of the first variation of the second embodiment of the guide tool is configured to drill holes for only the legs of one staple and another hole for a bone screw. The first variation of the second embodiment of the guide tool differs from that of the second embodiment in that it has a forward drill guide 316 that is fixed to an arm 318 such that its angle cannot be adjusted. The arm 318 has four segments, a first segment 320 extending forward from a rear set of drill guides 312 and a handle 314 to a first bend 322, a second segment 324 extending at an angle relative to the first segment 320 and between the first bend 322 a second, downward bend 326, a third segment 328 extending downward from the second bend 326 to a third, inward bend 330, and a fourth segment 332 extending inward from the third bend 330 to the forward drill guide 316. Of course, the number of bends and segments can be varied to achieve the same positioning between the drill guides 312 and 316. For example, the arm can be continuously or partially arcuate. The forward drill guide 316 can include an array of drill guides 317, such as two or, as shown, three arranged generally vertically relative to each other. Each of the drill guides 317 of the array of drill guides can optionally receive a cannulated guide 319, as shown in FIGS. 28-30, for use in insertion of a guide wire. The guide wire can be rotated, in a drilling manner, or otherwise inserted into the bone. Having an array of drill guides 317 allows for a user to select the relative position of the drilled or otherwise formed hole, for example, relative to the drilled holes for the staple made using the rearward drill guides 312.

The drill guides 317 optionally each include a lateral opening such that they have generally C-shaped cross section. The lateral opening can be useful during a procedure where a guide wire is used with the forward drill guide 316. For example, a procedure can include positing of the tool adjacent one or more bones, then inserting a guide wire into the bone via the drill guides 317 and guide 319. The guide 319 can then be slid off of the guide wire, opposite the insertion end of the wire, the arm 318 can then be decoupled relative to the handle 314 such that the handle 314 and rearward array of drill guides 312 remain in place. The guide wire can then pass through the lateral opening of the drill guide 317 so that the arm 318 can be removed, leaving the guide wire in place as well as the handle 314 and rearward array of drill guides 312. The rearward set of drill guides 312 can include apertures for guides wires for use in temporarily fixing the drill guides 312 relative to a bone or bones.

Figure 31:
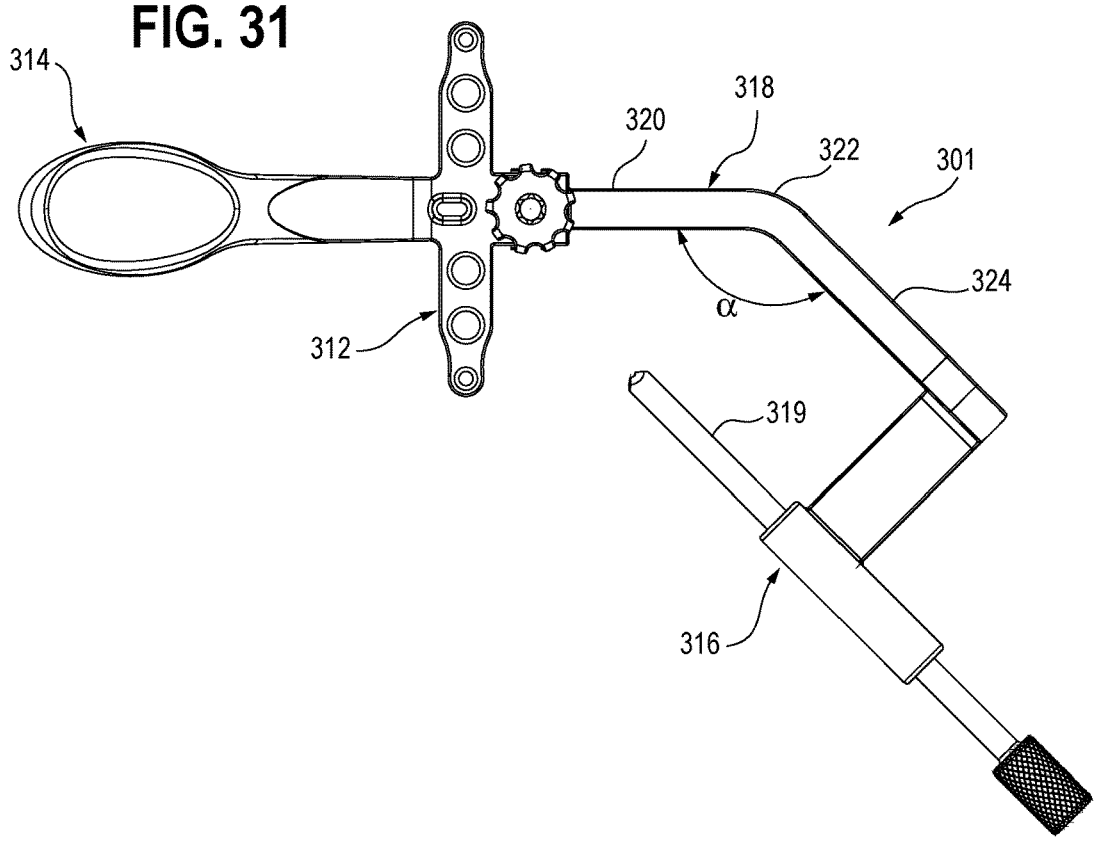
FIG. 31 is a top plan view of an alternative to the guide tool of FIG. 28, the with the forward guides being at a different angle compared to those of the guide tool of FIG. 28.
Figure 32:
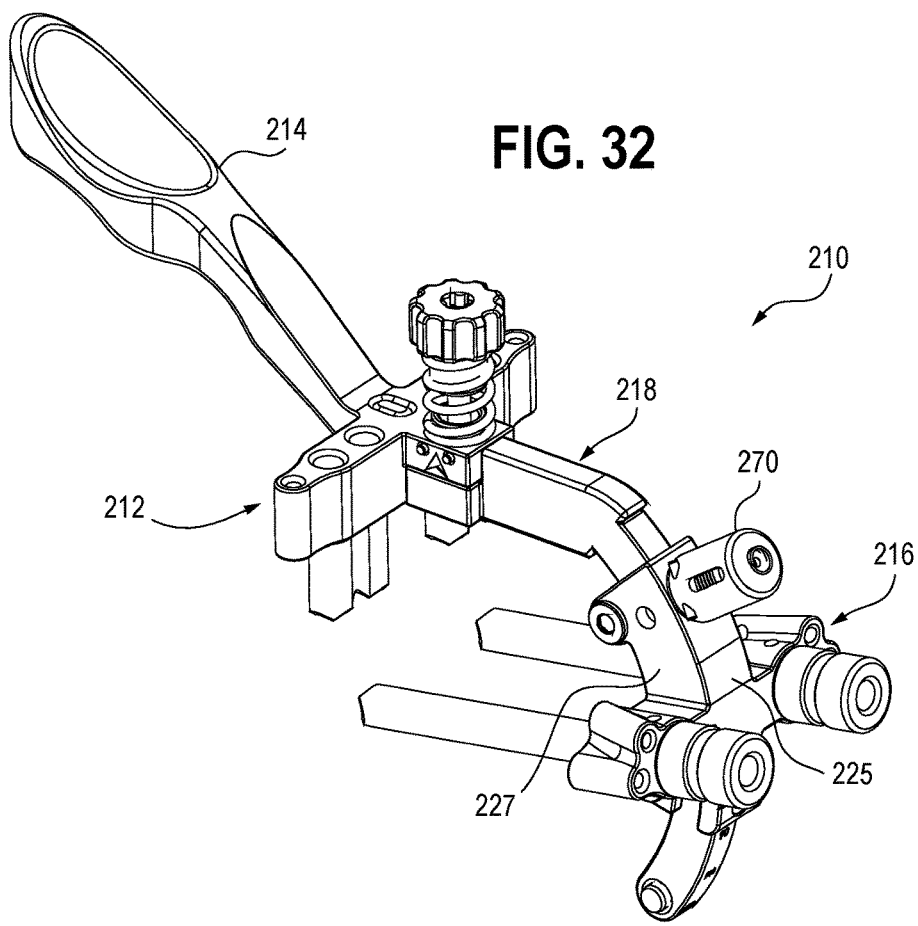
FIG. 32 is a perspective view of an alternative embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple.
Figure 33:
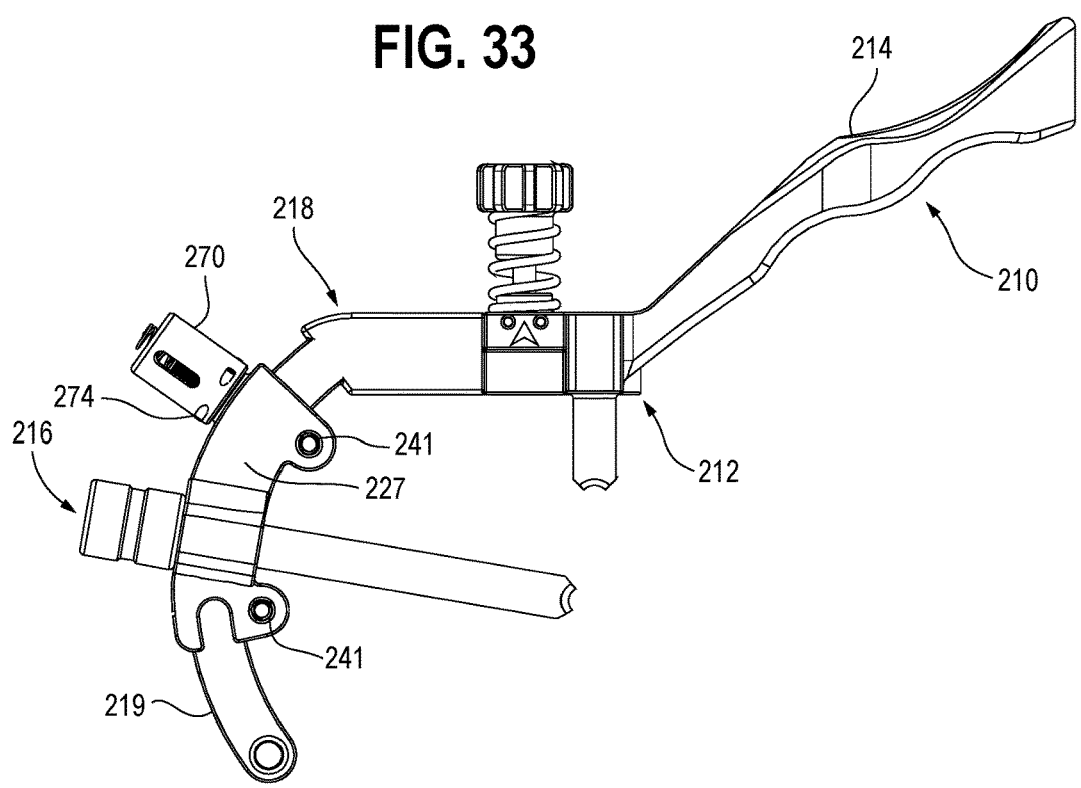
FIG. 33 is a left side elevation view of the guide tool of FIG. 32.
Figure 34:
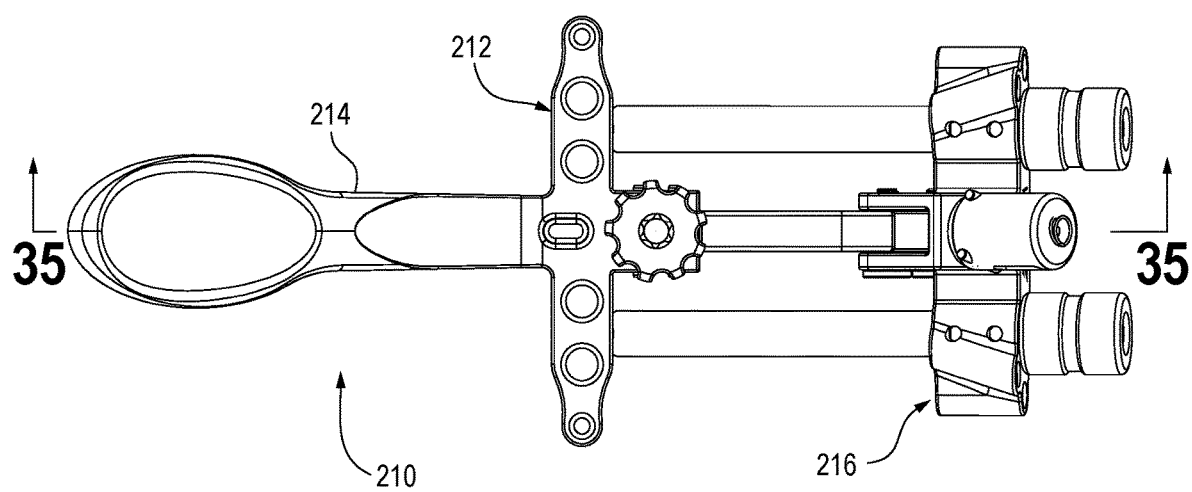
FIG. 34 is a top plan view of the guide tool of FIG. 32.

FIG. 31 shows a second variation of the second embodiment of the guide tool, with like parts having like numbers. The guide tool 301 difference as compared to the guide tool 300 of the first variation of the second embodiment, shown in FIGS. 28-30, in that the angle between the first and second segments of the arm extends oppositely.

The methods of using the first and second variation of the second embodiment of the guide tool are the same as described herein with respect to the second embodiment, with the exception that the forward drill guide is fixed to the arm such that the angle cannot be adjusted.

Figure 16:
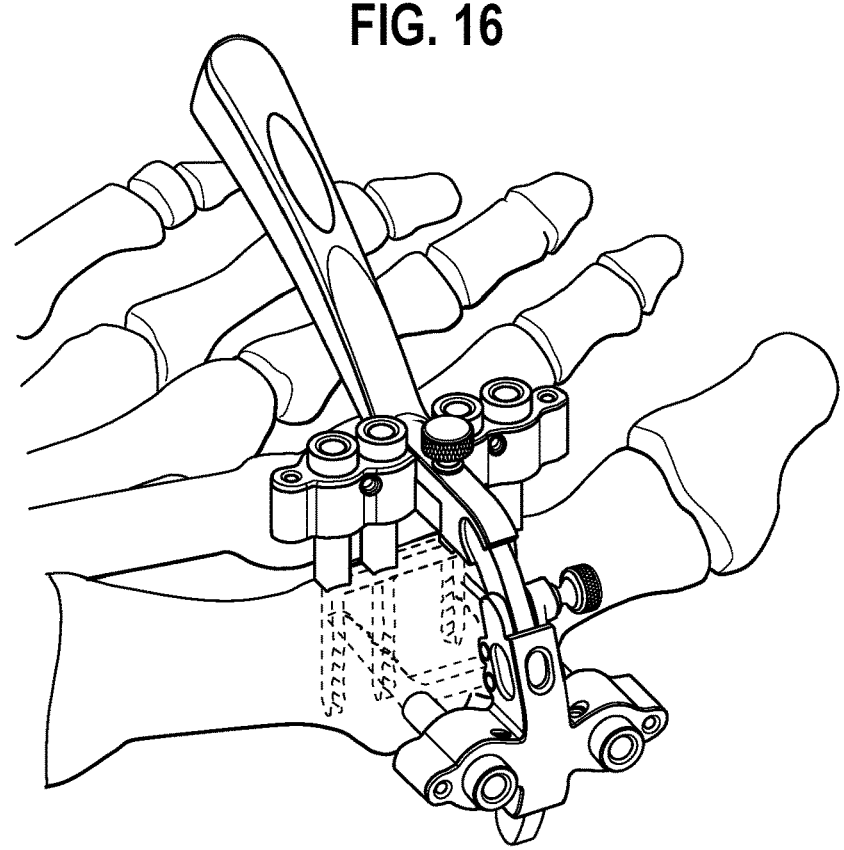
FIG. 16 is a perspective view of an alternative embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple, and having multiple openings through which guide pins can be inserted and passed into adjacent bones for positing the tool prior to the drilling of some or all of the guide holes.
Figure 17:
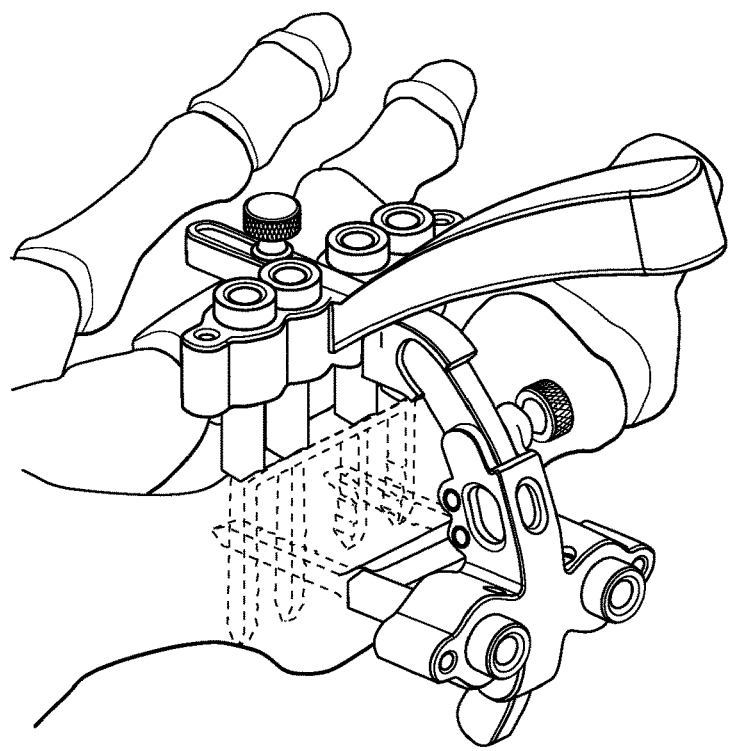
FIG. 17 is a perspective view of the tool of FIG. 16, showing guide holes having been drilled for the legs of the staples.

FIGS. 16 and 17 depict an alternative embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple. This embodiment differs from the first embodiment in that the handle is of a different size, the arm lacks the extension so that it can be inserted through a rear hole in the channel so that the handle is reversible, and there are multiple openings adjacent the drill guides through which guide pins can be inserted and passed into adjacent bones for positing the tool prior to the drilling of some or all of the guide holes. Any of these features can be incorporated into the other embodiments described herein. FIG. 17 shows guide holes having been drilled for the legs of the staples.

Figure 18:
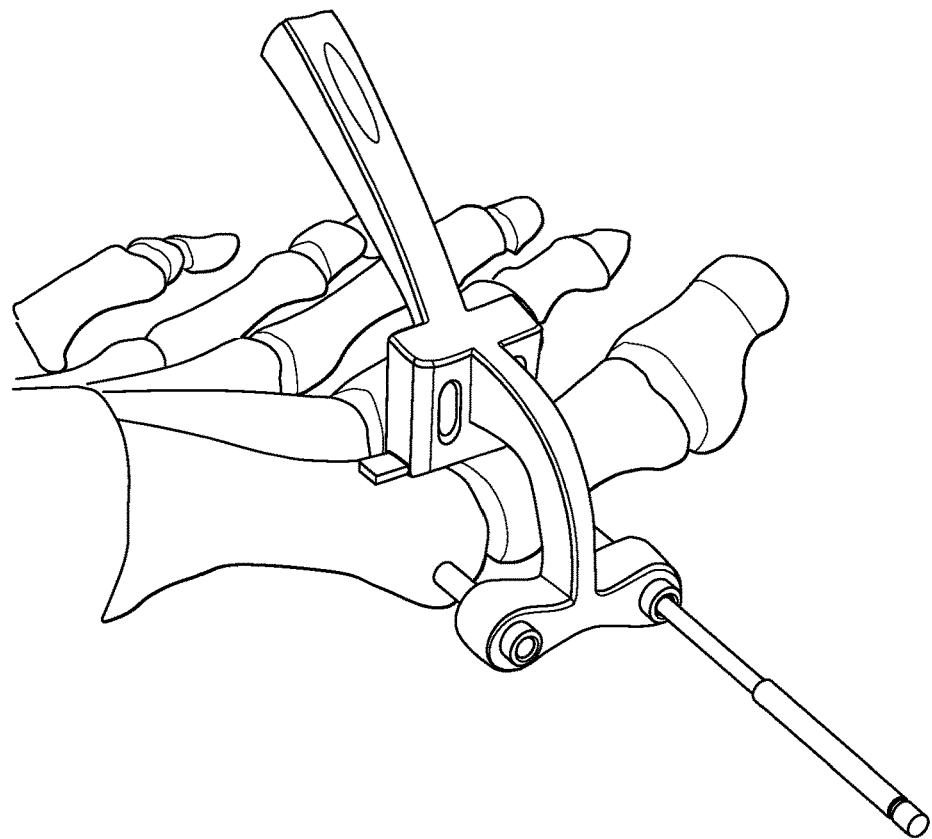
FIG. 18 is another alternative tool, having a portion that can clamp or at least partially anchor onto an already-inserted staple, and a forward portion with a pair of drilling guides.
Figure 19:
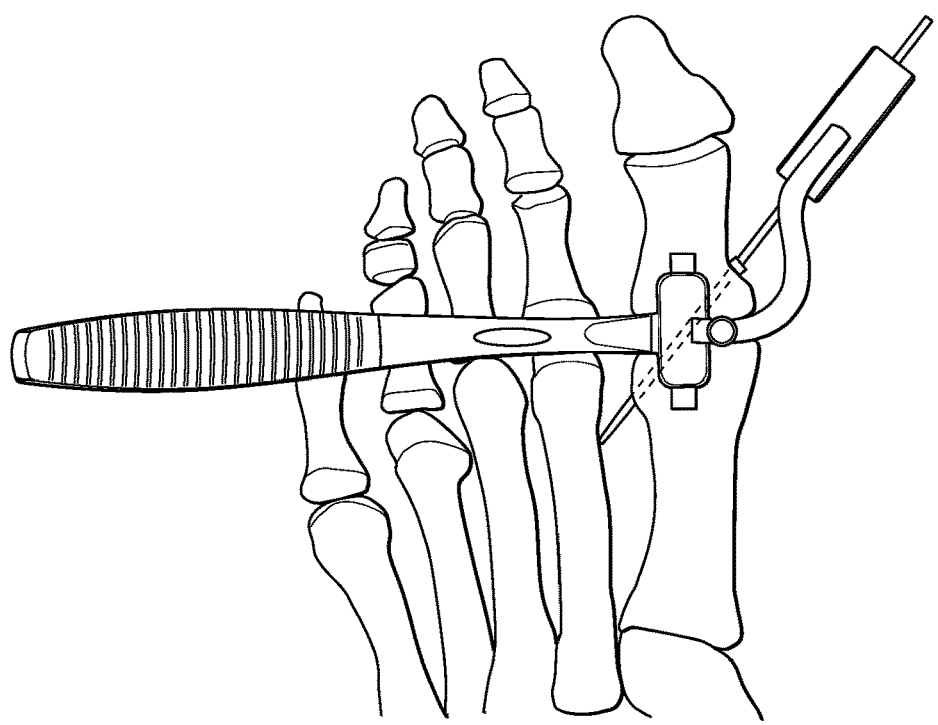
FIG. 19 is another alternative tool, having a portion that can clamp or at least partially anchor onto an already-inserted staple, and a forward portion with an offset drilling guide for drilling a guide hole for a screw.

FIGS. 18 and 19 depict additional alternative tools. Each of these two tools has a portion that can clamp or at least partially anchor onto an already-inserted staple, such as groove or slot for receiving the bridge of the staple. Each of these two tools also includes a forward portion with a pair of drilling guides (FIG. 18) for drilling guide holes for a staple, in the illustrated embodiment, a two-legged staple, or an offset drilling guide (FIG. 19) for drilling a guide hole for a screw.

Figure 24:
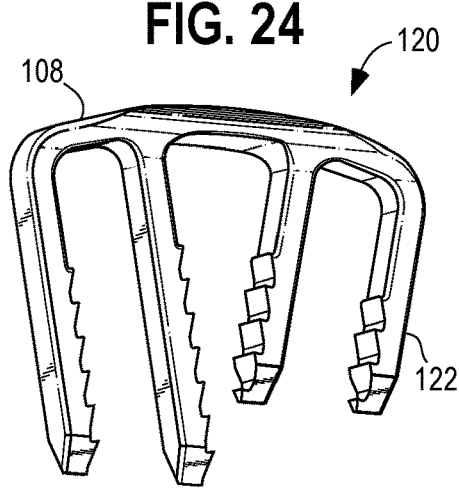
FIG. 24 is a perspective view of a surgical staple having four legs.
Figure 25:
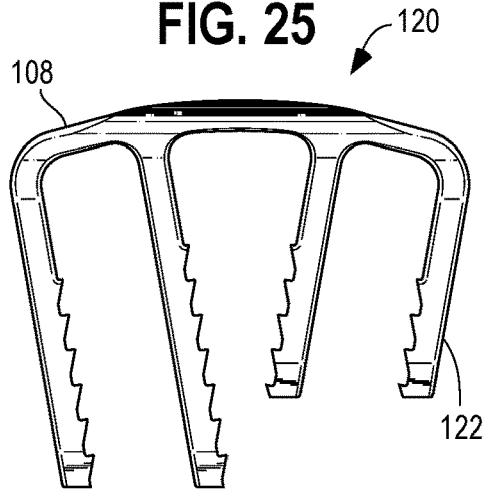
FIG. 25 is a side elevation view of the surgical staple of FIG. 22, showing legs of the staple at acute angle relative to a bridge.

FIGS. 20-25 disclose various embodiments of staples 100, 110, 120, some staples 110 with two legs 112 (FIGS. 20 and 21), some staples 100, 120 with four legs 102, 122 (FIGS. 22 and 23), and one 120 with four legs 122, two of which are shorter than the other two legs (FIGS. 24 and 25). The legs of the staples are connected via a bridge 104, 106, 108, and the legs can optionally have teeth such as those shown. The use of a staple with two legs shorter than another two legs can beneficially be used for various procedures, such as when one of the bones or the operative portion of the bone has a thickness that may not warrant or be suitable for a longer leg. Other shapes and sizes of staples can be used, such as those disclosed in U.S. patent application Ser. Nos. 29/804,413 and 29/804,411, each filed May 17, 2021, which are each hereby incorporated herein by reference in their entireties.

The staples are preferably, though not necessarily, made of nitinol or another shape memory material. Sleeves and arm can be made of surgical grade stainless steel, among other materials. The handle and bracket can also be made of surgical grade stainless steel, suitable thermoplastics, e.g., polyphenylsulfone (PPSU), or outer suitable materials.

As shown in the embodiments of FIGS. 28-37, the arms 218, 318 and the guides thereon can be removably coupled relative to the handles 218, 318 and the rearward drill guides associated therewith. This allows for the option during a procedure to decouple the rearward drill guides relative to the forward guide or guides. For example, the tool can be positioned and, optionally secured such as using one or more guide wires, and then the forward guide or guides can be used. The arm carrying the forward guide or guides can then be decoupled from the handle with the handle and associated rearward drill guide remaining in place for use during the procedure. In the illustrated examples, the arm has a rearward portion that engages with a forward portion of the handle. The rearward portion of the arm can be removed downward relative to the forward portion of the handle, or from an opposite side from the direction that the handle projects. Optionally, a protuberance of the rearward portion of the arm extends into an opening fixed relative to the handle. A screw can be used to clamp the arm and handle relative to each other, and the screw can optionally have a knurled knob and be spring biased away from engagement. A shaft of the screw can have an enlarged diameter area for forming a stop against an opening through which the shaft partially extends. Pins can be used to restrict removal of the screw such that the screw remains attached relative to the handle when the arm is decoupled. A bore in the rearward portion of the arm can include threading for receiving a threaded end of the screw.

In any of the foregoing embodiments, the components of the tools can optionally include one or more apertures for use with guide wires or the like to attach or position the tool or specific components thereof, such as the handle, rearward set of drill guides and/or forward drill guide or set of guides.

A handle that can be part of any of the foregoing embodiments is depicted in FIGS. 38-43.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A guide tool adapted for use in drilling holes in bones for insertion of legs of a first surgical staple and legs of a second surgical staple, the guide tool comprising:
    a handle;
    a rearward set of drill guides fixed relative to the handle; and
    an arm fixed relative to the handle, the arm having a forward set of drill guides,
    each of the forward set of drill guides has a longitudinally extending opening with a central axis, the longitudinally extending openings adapted for inserting a drill bit for drilling a hole in an adjacent bone; and
    each of the rearward set of drill guides has a longitudinally extending opening with a central axis, the longitudinally extending openings adapted for inserting a drill bit for drilling a hole in an adjacent bone;
    wherein one of the forward set of drill guides and rearward set of drill guides includes four drill guides and another of the forward set of drill guides and rearward set of drill guides includes two drill guides, and wherein the arm is configured such that the central axes of the two drill guides project between a projection of the central axes of the four drill guides.

2. The guide tool of claim 1, wherein the rearward set of drill guides includes four drill guides and the forward set of drill guides includes two drill guides, and wherein the arm is configured such that the central axes of the drill guides of the forward set of drill guides project between a projection of the central axes of the drill guides of the rearward set of drill guides.

3. The guide tool of claim 1, wherein a line passing through one of the central axes of the forward set of drill guides is at an angle of between 30° and 150° relative to a line passing through one of the central axes of the rearward set of drill guides.

4. The guide tool of claim 1, wherein each of the drill guides includes a sleeve with a through-bore for receiving, in use, a drill bit, the sleeves of the rearward set of drill guides being axially and rotationally fixed relative to the handle and the sleeves of the forward set of drill guides being axially and rotationally fixed relative to the handle.

5. The guide tool of claim 1, wherein the handle, at least a portion of the rearward set of drill guides and at least a portion of the forward set of drill guides are unitary and formed of a single body.

6. A method of drilling holes in one or more bones for insertion of a legs of a first surgical staple and legs of a second surgical staple using the guide tool of claim 1, the method comprising:
    positioning the rearward set of drill guides adjacent the bone or one of the bones;
    positioning the forward set of drill guides adjacent the bone or another of the bones;
    inserting a drill bit progressively through each of the drill guides of the rearward set of drill guides and drilling holes in the bone or one of the bones for receiving the legs of the first surgical staple; and
    inserting a drill bit progressively through each of the drill guides of the forward set of drill guides and drilling holes in the bone or another of the bones for receiving the legs of the second surgical staple.

7. A method of securing a first bone or bone piece to a second bone or bone piece using a first surgical staple having four legs and a second surgical staple having two legs, the method comprising:
    drilling a first set of holes in the first and second bone pieces or bones using a first set of drill guides, the first set of holes comprising four holes for receiving the legs of the first surgical staple, the four holes comprising a first pair of holes and a second pair of holes, at least one of the first set of holes being in the first bone and at least one of the first set of holes being in the second bone;
    drilling a second set of holes in the first and second bone pieces or bones using a second set of drill guides, the second set of holes comprising two holes for receiving the legs of the second surgical staple, one of the second set of holes being in the first bone and one of the second set of holes being in the second bone, wherein one of the two holes passes between the first pair of holes and another of the two holes passes between the second pair of holes;
    inserting the four legs of the first surgical staple in the four holes; and
    inserting the two legs of the second surgical staple in the two holes;
    wherein the first and second set of drill guides are permanently fixed relative to each other.

8. A guide tool adapted for use in drilling holes in bone pieces or bones for insertion of legs of a surgical staple and a bone screw, the tool comprising:
    a handle;
    a rearward set of drill guides fixed relative to the handle for use in drilling holes for the legs of the surgical staple, each of the rearward set of drill guides having a longitudinally extending opening with a central axis, the longitudinally extending openings adapted for insertion of a drill bit for drilling a hole in an adjacent bone;
    an arm extending forward relative to the handle; and
    a forward drill guide fixed relative to the arm for use in drilling a hole for the bone screw, the forward drill guide having a longitudinally extending opening with a central axis, the longitudinally extending opening adapted for inserting a drill bit for drilling a hole through a pair of adjacent bones or bone pieces;

wherein the arm has a plurality of bends such that the central axis of the forward drill guide projects between a projection of the central axes of the rearward set of drill guides and at an oblique angle relative to a line extending between each of the central axes of the rearward set of drill guides.

9. A method of drilling holes in bone pieces or bones for insertion of a legs of a surgical staple and bone screw using the guide tool of claim 8, the method comprising:

positioning the rearward set of drill guides and the forward drill guide adjacent the bones;

inserting a drill bit progressively through each of the drill guides of the rearward set of drill guides and drilling holes for the legs of the surgical staple in the bones; and inserting a drill bit through the forward drill guide and drilling a hole for the bone screw through one of the bones and at least partially into another of the bones.

\* \* \* \* \*